United States Patent
Belmant et al.

(10) Patent No.: US 7,767,842 B2
(45) Date of Patent: Aug. 3, 2010

(54) CLASS OF γδ T CELLS ACTIVATORS AND USE THEREOF

(75) Inventors: Christian Belmant, Six-Fours-les-Plages (FR); Patrice Nury, Hunzenschwil (CH)

(73) Assignee: Innate Pharma SA, Marseille (FR)

( * ) Notice: Subject to any disclaimer, the term of this patent is extended or adjusted under 35 U.S.C. 154(b) by 444 days.

(21) Appl. No.: 10/581,144

(22) PCT Filed: Dec. 2, 2004

(86) PCT No.: PCT/IB2004/004311

§ 371 (c)(1),
(2), (4) Date: Jul. 5, 2007

(87) PCT Pub. No.: WO2005/054258

PCT Pub. Date: Jun. 16, 2005

(65) Prior Publication Data

US 2007/0249565 A1    Oct. 25, 2007

Related U.S. Application Data

(63) Continuation-in-part of application No. PCT/IB03/006375, filed on Dec. 2, 2003.

(60) Provisional application No. 60/579,237, filed on Jun. 15, 2004.

(30) Foreign Application Priority Data

Dec. 2, 2002    (EP) .................................. 02292963

(51) Int. Cl.
C07F 9/22         (2006.01)
A61K 31/664    (2006.01)

(52) U.S. Cl. ........................ 558/199; 558/201; 514/137

(58) Field of Classification Search ................ 558/199, 558/201, 152; 514/137
See application file for complete search history.

(56) References Cited

U.S. PATENT DOCUMENTS

| 6,624,151 B1 | 9/2003 | Belmant et al. |
| 6,627,416 B1 | 9/2003 | Faulstich et al. |
| 7,399,756 B2 | 7/2008 | Jomaa et al. |
| 2006/0030546 A1 | 2/2006 | Jomaa et al. |
| 2006/0110746 A1 | 5/2006 | Andre et al. |
| 2006/0194755 A1 | 8/2006 | Romagne et al. |
| 2006/0241087 A1 | 10/2006 | Montero et al. |
| 2008/0253998 A1 | 10/2008 | Andre et al. |

FOREIGN PATENT DOCUMENTS

| DE | 198 15 864 A1 | 10/1999 |
| WO | WO 97/21452 | 6/1997 |
| WO | WO 00/18967 | 4/2000 |
| WO | WO 00/36152 | 6/2000 |
| WO | WO 02/083720 A2 | 10/2002 |
| WO | WO 2006/054177 | 5/2006 |
| WO | WO 2007/099117 | 9/2007 |

OTHER PUBLICATIONS

Mustaev et al. Proceedings of the National Academy of Sciences of the United States of America, 1994, 99, p. 12036-12040.*
Tsuhako et al. Bull. Chem. Soc. Jpn., 1981, 54, p. 289-290.*
Fox et al. J. Org. Chem., 2002, 67, p. 5009-5010.*
Patini et al. Chem. Rev. 1996, 96, p. 3147-3176.*
Parvin et al. Biochemistry, 1969, 8(4), p. 1748-1755.*
Sicard et al. Infection and Immunity, 2000, 68(8), p. 4375-4377.*
Cox et al. Vaccine, 1997, 15(3), p. 248-256.*
Madigan et al. Brock Biology of Microorganisms, 1997, Prentice Hall, 8th ed., p. 813-819.*
Database CA 'Online!, Chemical Abstracts Service, Database Accession No. 1967:440307, XP-002329669, p. 1.
Database CA 'Online!, Chemical Abstracts Service, Database Accession No. 1977:479963, XP-002329670, pp. 1-3.
Database CA 'Online!, Chemical Abstracts Service, Database Accession No. 1989:71465, XP-002329671, p. 1.
Database CA 'Online!, Chemical Abstracts Service, Database Accession No. 1995:112825, XP-002329672, pp. 1-2.
Database CA 'Online!, Chemical Abstracts Service, Database Accession No. 1995:258978, XP-002329673, pp. 1-8.
Database CA 'Online!, Chemical Abstracts Service, Database Accession No. 1995:371063, XP-002329674, pp. 1-3.
Database CA 'Online!, Chemical Abstracts Service, Database Accession No. 1999:61574, XP-002329675, pp. 1-2.
Database CA 'Online!, Chemical Abstracts Service, Database Accession No. 1999:646526, XP-002329676, pp. 1-3.

(Continued)

Primary Examiner—Shaojia Anna Jiang
Assistant Examiner—Jonathan S Lau
(74) Attorney, Agent, or Firm—Saliwanchik, Lloyd & Saliwanchik

(57) ABSTRACT

The present invention relates to a new class of compounds having γδ T cells activating properties of Formula (I),

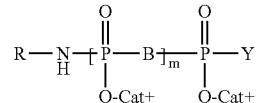

Formula I a composition comprising these compounds and methods for regulating an immune response in a subject comprising the step of administering these compounds.

14 Claims, 1 Drawing Sheet

OTHER PUBLICATIONS

Database CA 'Online!, Chemical Abstracts Service, Database Accession No. 2000:11855, XP-002329677, p. 1.

Database CA 'Online!, Chemical Abstracts Service, Database Accession No. 2001:799287, XP-002329678, pp. 1-3.

Database CA 'Online!, Chemical Abstracts Service, Database Accession No. 2001:823873, XP-002329679, pp. 1-2.

Database CA 'Online!, Chemical Abstracts Service, Database Accession No. 2002:371240, XP-002329680, pp. 1-2.

Database Beilstein Online!, Database Accession No. BRN 4287288, XP-002329874, p. 1.

Database Beilstein Online!, Database Accession No. BRN 7262054, XP-002329875, pp. 1-2.

Zwierzak, A. "Selective N-Alkylation of Diethyl Phosphoramidate: Tetrabutylaminium Bromide as Catalyst for Nucleophilic Substitution in a Homogeneous Medium" *Synthesis*, Nov. 1982, pp. 920-922, vol. 11.

Tanaka, Y. et al. "Natural and synthetic non-peptide antigens recognized by human gamma delta T cells" *Nature*, May 11, 1995, pp. 155-158, vol. 375, No. 6527.

Belmant, C. et al. "A chemical basis for selective recognition of nonpeptide antigens by human delta T cells" *FASEB J.*, Sep. 2000, pp. 1669-1670, vol. 14.

Valentijn, A.R.P.M. et al. "An expeditious synthesis of pyrophosphate analogues of farnesyl pyrophosphate using the phosphonylating agent methyl methylphosphonomorpholidate" *Synlett*, Sep. 1991, pp. 663-664.

Hintz, M. et al. "Identification of (*E*)-4-hydroxy-3-methyl-but-2-enyl pyrophosphate as a major activator for human gamma delta T cells in *Escherichia coil*" *FEBS Lett.*, 2001, pp. 317-322, vol. 509.

\* cited by examiner

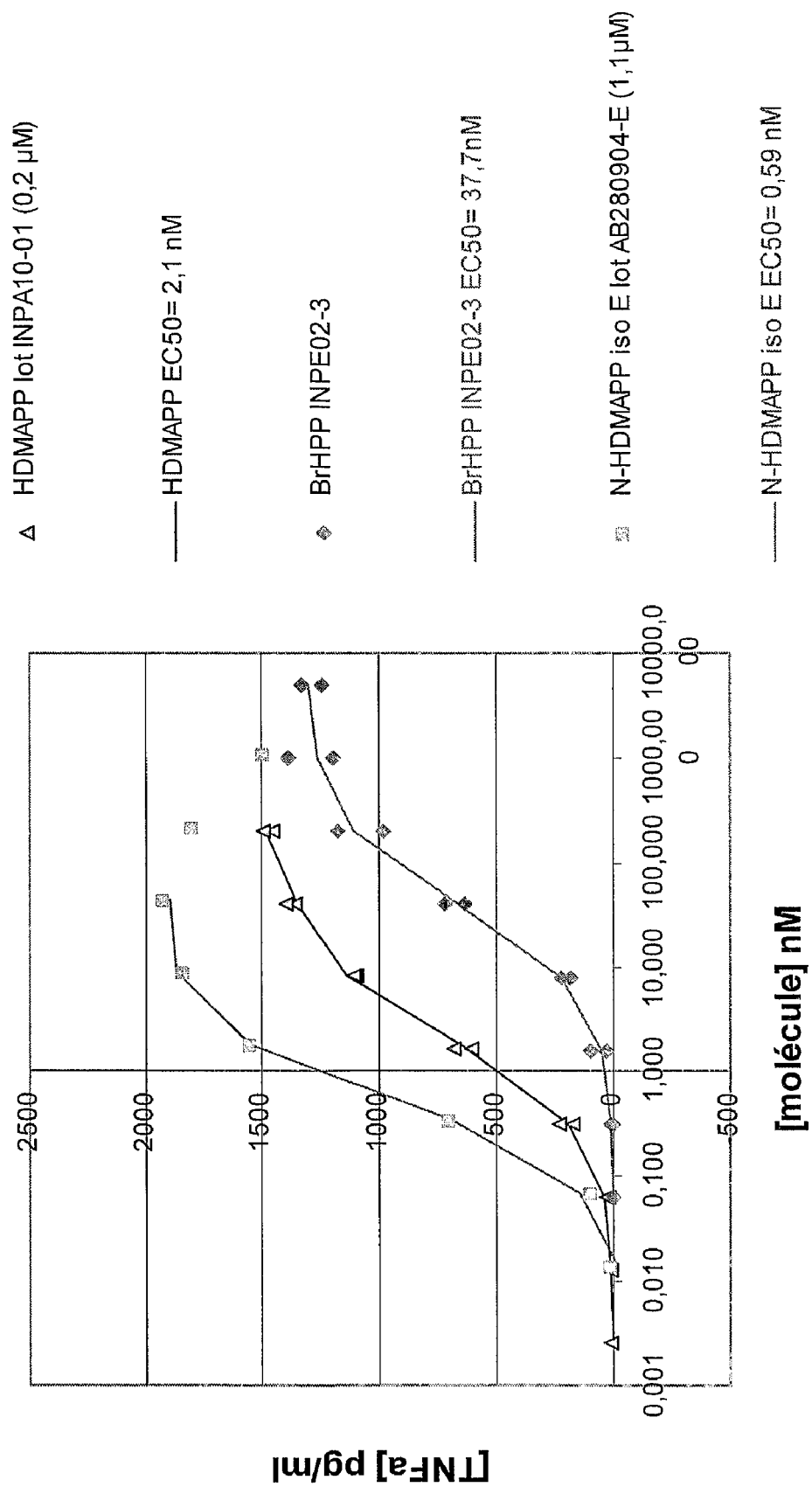

# CLASS OF γδ T CELLS ACTIVATORS AND USE THEREOF

CROSS-REFERENCE TO RELATED APPLICATION

This application is the U.S. national stage application of International Patent Application No. PCT/IB2004/004311, filed Dec. 2, 2004 which is a continuation-in-part of International Patent Application No. PCT/IB2003/006375, filed Dec. 2, 2003. International Patent Application No. PCT/IB2004/004311, filed Dec. 2, 2004, claims the benefit of U.S. Provisional Patent Application No. 60/579,237, filed Jun. 15, 2004. The disclosures of each of these applications are hereby incorporated by reference in their entireties, including all figures, tables and amino acid or nucleic acid sequences.

FIELD OF THE INVENTION

The present invention relates to a new class of compounds having γδ T cells activating properties, a composition comprising these compounds and methods for regulating an immune response in a subject comprising the step of administering these compounds.

BACKGROUND

Most human peripheral blood γδ T cells express a γδTCR heterodimer encoded by Vγ9/Vδ2 genes, some NK-lineage receptors for MHC class I and almost no CD4 nor CD8. These cells have been shown to exhibit strong, non MHC-restricted, cytolytic activity against virus-infected cells (Poccia et al (1999), parasite-infected cells (Constant et al (1995)), or tumor cells (Fournie et Bonneville (1996)). These cells are also physiologically amplified in the context of several unrelated infectious diseases such as tuberculosis, malaria, tularemia, colibacillosis and also by B-cell tumors (for review see Hayday, 2000).

Beside their anti-infectious activity, it was shown in short term cytotoxicity assays that Vγ9/Vδ2 T cells are able to lyse a wide variety of tumor cell lines from very diverse origins: lymphoma and leukemia from B-cell, T-cell or myeloid lineages (Fisch et al., 1997; Selin et al., 1992; Sicard et al., 2001; Sturm et al., 1990; Zheng et al., 2001a), breast carcinoma (Bank et al., 1993), glioblastoma (Fujimiya et al., 1997; Yamaguchi et al., 1997), renal cell carcinoma (Choudhary et al., 1995; Kobayashi et al., 2001; Mitropoulos et al., 1994), nasopharyngeal carcinoma (Zheng et al., 2001b), lung adenocarcinoma (Ferrarini et al., 1996).

In microbes, Vγ9/Vδ2+ lymphocytes spontaneously recognize a structurally related set of nonpeptide antigens, referred to as natural phosphoantigens and alkylamines. In B cell tumors, the nature of antigens for the γδ T cells remains unidentified. Vγ9/Vδ2+ lymphocytes are also responsive to a variety of virally infected-, activated- or tumoral cell types without prior exposure. Again, in these situations, the responsible antigens remain unknown (for review see Fisch, 2000). It has been shown that, in vitro, Vγ9/Vδ2 2+ lymphocytes respond to synthetic drugs such as therapeutic aminobisphosphonates (reviewed in Espinosa, 2001), leading to their in vitro activation. Recognition of natural non-peptide antigens is mediated by the γδ TCR, through amino acid residues located on both Vγ9- and Vδ2-CDR3 regions. Although neither processing nor presentation by CD1 or MHC molecules is involved, Vγ9/Vδ2+ lymphocyte activation by non-peptide antigens appears to require cell-to-cell contact (Lang, 1995; Morita, 1995; Miyagawa, 2001, Rojas, 2002).

The stimulating bacterial antigens have been shown to be small non peptidic compounds classically referred to as phosphoantigens (Behr et al., 1996; Belmant et al., 2000; Constant et al., 1994; Poquet et al., 1998; Tanaka et al., 1995), owing to the presence of phosphate groups in most instances.

Vγ9/Vδ2 T cells can also be activated through endogenous metabolites (acting in the micromolar range) such as isopentenyl pyrophosphate or IPP (Espinosa et al., 2001b; Tanaka et al., 1995), which is produced through the conventional mevalonate pathway shared by both microorganisms and mammalian cells. Production of IPP in the latter cells can be upregulated in situations of cell stress and transformation. In particular a recent study has reported a correlation between the endogenous production levels of IPP in tumor cells and their susceptibility to Vγ9/Vδ2 T cell-mediated lysis (Gober et al., 2003).

Also consistent with a direct contribution of endogenous metabolites of the mevalonate pathway to Vγ9/Vδ2 T cell recognition, cell treatment with pharmacological agents preventing IPP biosynthesis (such as statins) or leading to IPP accumulation (such as aminobisphosphonates, see below) lead respectively to decreased or enhanced Vγ9/Vδ2 T cell stimulating properties of the treated cells (Gober et al., 2003; Kato et al., 2001).

Aminobisphosphonates are thought to inhibit FPP synthase, an enzyme in the mevalonate pathway, the inhibition of which causes the accumulation and release of upstream isoprenoid lipids such as IPP. Aminobisphosphonate compounds had been used in human therapy for the treatment of bone metastases in cancer patients, and provided a first set of evidence for in vivo expansion of human Vγ9/Vδ2+ lymphocytes induced by phosphoantigen agonists, reporting increases of circulating 75 T cells within one to three weeks in human adults with multiple myeloma after therapeutic intravenous injection of 60-90 mg of pamidronate (Kunzmann et al, 1999). However, such compounds require presentation by antigen presenting cells and cannot produce substantial stimulation of Vγ9/Vδ2 T cell activity as assessed by cytokine secretion in a pure Vγ9/Vδ2 T cell culture. Moreover, pamidronate shows very low potency of activation of γδ T cells, reported to achieve at best only 2-fold increase in γδ T cell count (Wilhelm et al., 2003).

Recently, several highly potent γδ T cell activating pyrophosphate-containing compounds have been described which directly activate γδ T cells. In particular, phosphalohydrin and phosphoepoxyde compounds were described by the group of J. J. Fournie. (R,S)-3-(bromomethyl)-3-butanol-1-yl-diphosphate, also referred to as BrHPP (BromoHydrin PyroPhosphate) is currently used in ongoing human clinical studies to stimulate the proliferation of γδ T cells ex vivo. Other pyrophosphate containing compounds with high specific activity (EC50 in the nanomolar or better range) are produced through an isoprenoid biosynthetic pathway called the "Rohmer" or "non-mevalonate" pathway, which is specific to pro- and eukaryotic microorganisms (Feurle et al., 2002; Jomaa et al (2003); Jomaa et al., 1999a; Jomaa et al., 1999b; Rohmer et al., 1993).

Despite the foregoing, there is still a need of new compounds providing γδ T cell activation, in particular compounds having increased potency and/or preferred pharmacodynamic properties. Such compounds have particular advantages in non-life threatening or chronic therapeutic indications where therapies should be free of toxicity.

SUMMARY OF THE INVENTION

The present invention now discloses a new class of compounds having γδ T cell activating properties. This new class of compounds comprises phosphoramidate esters. The inventors have found that the class of compounds described herein have increased potency over other compounds that modulate γδ T cell activity previously tested by the inventors. In addition, the compounds can achieve a greater γδ T cell activating effect at their EC100 (the efficient concentration of the composition which produces its maximum response or effect with respect to such activity of γδ T cells) that other compounds.

These compounds can be used to efficiently regulate the activity of γδ T cells, particularly the activation and proliferation of γδ T cells, preferably Vγ9/Vδ2 T cells, in vivo in a subject. These new γδ T cell activators can be used in accordance with any of the methods described herein. These compounds are particularly suited for immunotherapy, particularly to treat a subject having a tumor or a subject suffering from other diseases, particularly an infectious disease, an autoimmune disease or an allergic disease. Compounds according to the present invention can also be used as a vaccine adjuvant.

In one aspect the invention provides a compound (γδ T cell activator) of formula (I):

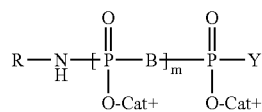

Formula (I)

wherein Cat+ represents one (or several, identical or different) organic or mineral cation(s) (including proton);

m is an integer from 1 to 3;

B is O, NH, or any group capable to be hydrolyzed;

Y=O⁻Cat+, a $C_1$-$C_3$ alkyl group, a group -A-R, or a radical selected from the group consisting of a nucleoside, an oligonucleotide, a nucleic acid, an amino acid, a peptide, a protein, a monosaccharide, an oligosaccharide, a polysaccharide, a fatty acid, a simple lipid, a complex lipid, a folic acid, a tetrahydrofolic acid, a phosphoric acid, an inositol, a vitamin, a co-enzyme, a flavonoid, an aldehyde, an epoxyde and a halohydrin;

A is O, NH, CHF, $CF_2$ or $CH_2$; and,

R is a linear, branched, or cyclic, aromatic or not, saturated or unsaturated, $C_1$-$C_{50}$ hydrocarbon group, optionally interrupted by at least one heteroatom, wherein said hydrocarbon group comprises an alkyl, an alkylenyl, or an alkynyl, preferably an alkyl or an alkylene, which can be substituted by one or several substituents selected from the group consisting of: an alkyl, an alkylenyl, an alkynyl, an epoxyalkyl, an aryl, an heterocycle, an alkoxy, an acyl, an alcohol, a carboxylic group (—COOH), an ester, an amine, an amino group (—NH₂), an amide (—CONH₂), an imine, a nitrile, an hydroxyl (—OH), an aldehyde group (—CHO), an halogen, an halogenoalkyl, a thiol (—SH), a thioalkyl, a sulfone, a sulfoxide, and a combination thereof.

In a preferred embodiment, said activator is a compound of formula (X):

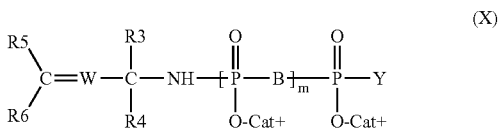

in which $R_3$, $R_4$, and $R_5$, identical or different, are a hydrogen or ($C_1$-$C_3$)alkyl group, W is —CH— or —N—, $R_6$ is an ($C_2$-$C_3$)acyl, an aldehyde, an ($C_1$-$C_3$)alcohol, or an ($C_2$-$C_3$) ester, Cat+ represents one (or several, identical or different) organic or mineral cation(s) (including the proton), B is O or NH, m is an integer from 1 to 3, and Y is O⁻Cat+, a nucleoside, or a radical -A-R, wherein A is O, NH, CHF, $CF_2$ or $CH_2$, and R is selected from the group consisting of 1), 2) or 3).

In a father aspect, said activator is a compound selected from the group consisting of:

formula (XI):

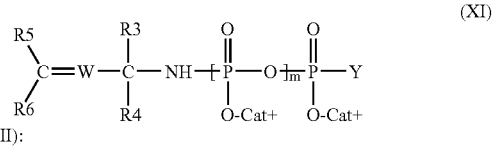

formula (XII):

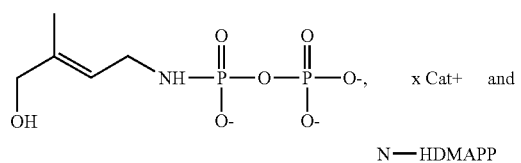

formula (II):

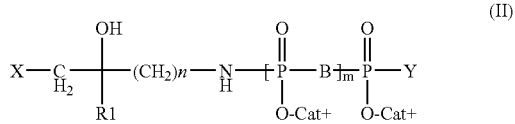

wherein in said formulas II, XI and XII: X is an halogen (preferably selected from I, Br and Cl), B is O or NH, m is an integer from 1 to 3, R1 is a methyl or ethyl group, Cat+ represents one (or several, identical or different) organic or mineral cation(s) (including the proton), and n is an integer from 2 to 20, and Y is O⁻Cat+, a nucleoside, or a radical -A-R, wherein A is O, NH, CHF, $CF_2$ or $CH_2$ and R is selected from the group consisting of 1), 2) or 3).

In further embodiments, the γδ T cell activator is a compound of formula (III)

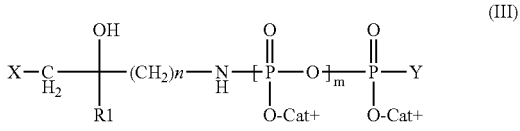

In further embodiments, the γδ T cell activator is a compound of formula (V)

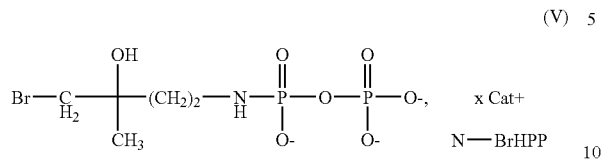

(V) N—BrHPP

In further embodiments, the γδ T cell activator is a compound of formula (VI):

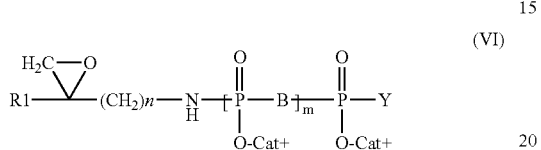

(VI)

in which R1 is a methyl or ethyl group, Cat+ represents one (or several, identical or different) organic or mineral cation(s) (including the proton), B is O or NH, m is an integer from 1 to 3, and n is an integer from 2 to 20, and Y is O⁻Cat+, a nucleoside, or a radical -A-R, wherein A is O, NH, CHF, $CF_2$ or $CH_2$, and R is selected from the group consisting of 1), 2) or 3).

The present invention also provides pharmaceutical composition comprising a γδ T cell activator according to any one of the embodiments described herein. Also provided are methods of modulating, preferably activating, a γδ T cell, the method comprising bringing a γδ T cell into contact with a γδ T cell activating compound described herein. As will be appreciated, compounds of the invention may be used to activate γδ T cell in vitro or in vivo. Activated γδ T cell in vitro may be used in any suitable method following activation, including in therapy or prevention of disease. In one preferred example activated γδ T cells are administered to a mammal, preferably a human. In a preferred aspect, the invention encompasses a method of treatment comprising (a) bringing a γδ T cell into contact with a γδ T cell activating compound described herein and (b) administering γδ T cells of step (a) to a subject. Methods for preparing γδ T cells for such applications are known in the art, for example can be carried out as described U.S. Ser. No. 10/505,252, filed August 19$^{th}$ and 2004 PCT/FR 03/00585 filed Feb. 21, 2003, both by Romagne and Laplace, the disclosures of which are incorporated herein by reference.

Also provided are methods of modulating, preferably activating a γδ T cell comprising administering to a subject a γδ T cell activator described herein. In preferred embodiments, the inventions provides a method for treating or preventing a disease comprising administering to a subject a γδ T cell activator described herein in an amount sufficient to ameliorate or prevent said disease. Also provided is the use of a γδ T cell activator of the invention for the manufacture of a pharmaceutical composition for regulating γδ T cells in a human subject. Preferably said disease is a tumor or proliferative disorder, an infectious disease, an autoimmune disease or an allergic disease.

The invention further provides methods for the synthesis of phosphoroamidate compounds. In one aspect the invention provides a method for preparing a diphosphoramidate monoester compound comprising:

(a) reacting an alkylhalide R—X in a coupling step with a diethylphosphoramidate or diethylchlorophosphate reagent;
(b) reacting the compound prepared in step (a) in a saponification step thereby removing O-ethyl groups; and
(c) reacting the compound prepared in step (b) in a phosphorylation step thereby preparing a diphosphoramidate monoester, wherein R is a linear, branched, or cyclic, aromatic or not, saturated or unsaturated, C1-C50 hydrocarbon group, optionally interrupted by at least one heteroatom, wherein said hydrocarbon group comprises an alkyl, an alkylenyl, or an alkynyl, preferably an alkyl or an alkylene, which can be substituted by one or several substituents selected from the group consisting of: an alkyl, an alkylenyl, an alkynyl, an epoxyalkyl, an aryl, an heterocycle, an alkoxy, an acyl, an alcohol, a carboxylic group (—COOH), an ester, an amine, an amino group (—NH2), an amide (—CONH2), an imine, a nitrile, an hydroxyl (—OH), a aldehyde group (—CHO), an halogen, an halogenoalkyl, a thiol (—SH), a thioalkyl, a sulfone, a sulfoxide, and a combination thereof, and wherein X is a moiety capable of being displaced by a diethylphosphoramidate group under suitable conditions. Depending on the type and reactivity of the functional groups provided by R, the professional is able to adapt the following examples, if necessary including the phases of protection/deprotection of the sensitive functional groups or those that can interact with the coupling reaction. In one embodiment X is an NH2 group and said R—X compound is reacted in a coupling step with a diethylchlorophosphate compound. In another embodiment, X is selected from the group consisting of I, Br and Cl. In another aspect the invention provides a method of preparing a (E)-2-(4-azido-2-methylbut-2-en yloxy)tetrahydro-2H-pyran compound, comprising providing a (E)-2-(4-Chloro-2-methylbut-2-en yloxy)tetrahydro-2H-pyran compound and reacting said compound with a sodium azide in a water-pentane biphasic mixture in the presence of phase transfer catalyst.

Additional embodiments and details are father provided herein.

DESCRIPTION OF THE DRAWINGS

FIG. 1 shows an in vitro dose response curve and EC50 values for compound of the invention N-HDMAPP and reference compounds BrHPP and HDMAPP. The compound of the invention demonstrates not only 3-4 fold increased potency over the next most potent compounds, but also increased absolute activation of γδ T cells as observed by TNFα release.

DETAILED DESCRIPTION

Definitions

Within the context of the present invention, the expression "regulating the activity of γδ T cells" designates causing or favoring an increase in the number and/or biological activity of such cells in a subject. Regulating thus includes without limitation modulating (e.g., stimulating) expansion of such cells in a subject and/or, for instance, triggering of cytokine secretion (e.g., TNFα or IFNγ). As indicated, γδ T cells normally represent between about 1-10% of total circulating lymphocytes in a healthy adult human subject. The present invention can be used to significantly increase the γδ T cells population in a subject, particularly to reach at least 10%, 12%, 15%, 20%, or 30-90% of total circulating lymphocytes, typically 40-90%, more preferably from 50-90%. In typical embodiments, the invention allows the selective expansion of γδ T cells in a subject, to reach 60-90% of total circulating lymphocytes, preferably 70-90%, more preferably from 80-90%. Regulating also includes, in addition or in the alternative, modulating the biological activity of γδ T cells in a subject, particularly their cytolytic activity or their cytokine-secretion activity. The invention defines novel conditions and strategies for increasing the biological activity of γδ T cells towards target cells.

Where "comprising" is used, this can preferably be replaced by "consisting essentially of", more preferably by "consisting of".

Where hereinbefore and hereinafter numerical terms are used, they are meant to include the numbers representing the upper and lower limits. For example, "between 1 and 3" stands for a range "from and including 1 up to and including 3", and "in the range from 1 to 3" would stand for "from and including 1 up to and including 3". The same is true where instead of numbers (e.g. 3) words denoting numbers are used (e.g. "three").

Where "about" is used in connection with a number, this preferably means the number +/−1-15%, more preferably the number plus 5%, most preferably the number itself without "about". For example, "about 100" would stand for "from and including 85 to and including 115". Where "about" is used in connection with numeric ranges, for example "about 1 to about 3", or "between about one and about three", preferably the definition of "about" given for a number in the last sentence is applied to each number defining the start and the end of a range separately. Preferably, where "about" is used in connection with any numerical values, the "about" can be deleted.

"Weekly" stands for "about once a week" (meaning that more than one treatment is made with an interval of about one week between treatments), the about here preferably meaning +/−1 day (that is, translating into "every 6 to 8 days"); most preferably, "weekly" stands for "once every 7 days".

As used herein, the term "EC50" with respect to regulating the activity of γδ T cells, refers to the efficient concentration of the subject compositions which produces 50% of its maximum response or effect with respect to such activity of γδ T cells.

As used herein, the term "EC100" with respect to regulating the activity of γδ T cells, refers to the efficient concentration of the subject compositions which produces its maximum response or effect with respect to such activity of γδ T cells.

New Class of γδ T Lymphocyte Activators: Phosphoramidate Esters

The new class of compounds described by the present inventors comprises phosphoramidate esters. The inventors have found that the compounds of this class show increased in potency over other compounds that modulate γδ T cell activity previously tested by the inventors. In addition, the compounds of the invention can achieve greater γδ T cell activating effect at their EC100 (the efficient concentration of the composition which produces its maximum response or effect with respect to such activity of γδ T cells) than other compounds. While not wishing to be held by theory, the present inventors propose that the presence of an NH group may result in modified binding—generally increased strength of binding—to the compound's target, probably due to H-binding considerations compared for example to pyrophosphate ester compounds. This modification in H binding considerations can provide distinct pharmacological properties, for example target binding affinity, ADME properties (absorption, distribution, metabolism and excretion). In further preferred embodiment, the compounds of the invention also have desirable in vivo stability properties, preferably greater half-life than other available compounds. Increased stability in blood may be useful to achieve an improved overall vivo γδ T cell stimulation The new class of γδ T lymphocyte activators according to the present invention comprises the compounds of formula (I):

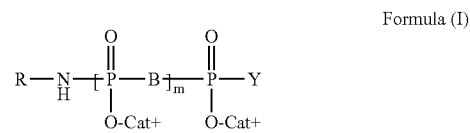

Formula (I)

wherein Cat+ represents one (or several, identical or different) organic or mineral cation(s) (including proton);

m is an integer from 1 to 3;

B is O, NH, or any group capable to be hydrolyzed;

Y=O⁻Cat+, a $C_1$-$C_3$ alkyl group, a group -A-R, or a radical selected from the group consisting of a nucleoside, an oligonucleotide, a nucleic acid, an amino acid, a peptide, a protein, a monosaccharide, an oligosaccharide, a polysaccharide, a fatty acid, a simple lipid, a complex lipid, a folic acid, a tetrahydrofolic acid, a phosphoric acid, an inositol, a vitamin, a co-enzyme, a flavonoid, an aldehyde, an epoxyde and a halohydrin;

A is O, NH, CHF, $CF_2$ or $CH_2$; and,

R is a linear, branched, or cyclic, aromatic or not, saturated or unsaturated, $C_1$-$C_{50}$ hydrocarbon group, optionally interrupted by at least one heteroatom, wherein said hydrocarbon group comprises an alkyl, an alkylenyl, or an alkynyl, preferably an alkyl or an alkylene, which can be substituted by one or several substituents selected from the group consisting of: an alkyl, an alkylenyl, an alkynyl, an epoxyalkyl, an aryl, an heterocycle, an alkoxy, an acyl, an alcohol, a carboxylic group (—COOH), an ester, an amine, an amino group (—NH$_2$), an amide (—CONH$_2$), an imine, a nitrile, an hydroxyl (—OH), a aldehyde group (—CHO), an halogen, an halogenoalkyl, a thiol (—SH), a thioalkyl, a sulfone, a sulfoxide, and a combination thereof.

In a particular embodiment, the substituents as defined above are substituted by at least one of the substituents as specified above.

Preferably, the substituents are selected from the group consisting of: an ($C_1$-$C_6$)alkyl, an ($C_2$-$C_6$)alkylenyl, an ($C_2$-$C_6$)alkynyl, an ($C_2$-$C_6$)epoxyalkyl, an aryl, an heterocycle, an ($C_1$-$C_6$)alkoxy, an ($C_2$-$C_6$)acyl, an ($C_1$-$C_6$)alcohol, a carboxylic group (—COOH), an ($C_2$-$C_6$)ester, an ($C_1$-$C_6$)amine, an amino group (—NH$_2$), an amide (—CONH$_2$), an ($C_1$-$C_6$) imine, a nitrile, an hydroxyl (—OH), a aldehyde group (—CHO), an halogen, an ($C_1$-$C_6$)halogenoalkyl, a thiol (—SH), a ($C_1$-$C_6$)thioalkyl, a ($C_1$-$C_6$)sulfone, a ($C_1$-$C_6$)sulfoxide, and a combination thereof.

More preferably, the substituents are selected from the group consisting of: an ($C_1$-$C_6$)alkyl, an ($C_2$-$C_6$)epoxyalkyl, an ($C_2$-$C_6$)alkylenyl, an ($C_1$-$C_6$)alkoxy, an ($C_2$-$C_6$)acyl, an ($C_1$-$C_6$)alcohol, an ($C_2$-$C_6$)ester, an ($C_1$-$C_6$)amine, an ($C_1$-

$C_6$)imine, an hydroxyl, a aldehyde group, an halogen, an ($C_1$-$C_6$)halogenoalkyl, and a combination thereof.

Still more preferably, the substituents are selected from the group consisting of: an ($C_3$-$C_6$)epoxyalkyl, an ($C_1$-$C_3$) alkoxy, an ($C_2$-$C_3$)acyl, an ($C_1$-$C_3$)alcohol, an ($C_2$-$C_3$)ester, an ($C_1$-$C_3$)amine, an ($C_1$-$C_3$)imine, an hydroxyl, an halogen, an ($C_1$-$C_3$)halogenoalkyl, and a combination thereof. and a combination thereof. Preferably, R is a ($C_3$-$C_{25}$)hydrocarbon group, more preferably a ($C_5$-$C_{10}$)hydrocarbon group.

In the context of the present invention, the term "alkyl" more specifically means a group such as methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl and the other isomeric forms thereof. ($C_1$-$C_6$)alkyl more specifically means methyl, ethyl, propyl, isopropyl, butyl, isobutyl, tert-butyl, pentyl, hexyl and the other isomeric forms thereof. ($C_1$-$C_3$)alkyl more specifically means methyl, ethyl, propyl, or isopropyl.

The term "alkenyl" refers to an alkyl group defined hereinabove having at least one unsaturated ethylene bond and the term "alkynyl" refers to an alkyl group defined hereinabove having at least one unsaturated acetylene bond. ($C_2$-$C_6$)alkylene includes a ethenyl, a propenyl (1-propenyl or 2-propenyl), a 1- or 2-methylpropenyl, a butenyl (1-butenyl, 2-butenyl, or 3-butenyl), a methylbutenyl, a 2-ethylpropenyl, a pentenyl (1-pentenyl, 2-pentenyl, 3-pentenyl, 4-pentenyl), an hexenyl (1-hexenyl, 2-hexenyl, 3-hexenyl, 4-hexenyl, 5-hexenyl), and the other isomeric forms thereof. ($C_2$-$C_6$)alkynyl includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl and the other isomeric forms thereof.

The term "epoxyalkyl" refers to an alkyl group defined hereinabove having an epoxide group. More particularly, ($C_2$-$C_6$)epoxyalkyl includes epoxyethyl, epoxypropyl, epoxybutyl, epoxypentyl, epoxyhexyl and the other isomeric forms thereof. ($C_2$-$C_3$)epoxyalkyl includes epoxyethyl and epoxypropyl.

The "aryl" groups are mono-, bi- or tri-cyclic aromatic hydrocarbons having from 6 to 18 carbon atoms. Examples include a phenyl, α-naphthyl, β-naphthyl or anthracenyl group, in particular.

"Heterocycle" groups are groups containing 5 to 18 rings comprising one or more heteroatoms, preferably 1 to 5 endocyclic heteroatoms. They may be mono-, bi- or tri-cyclic. They may be aromatic or not. Preferably, and more specifically for $R_5$, they are aromatic heterocycles. Examples of aromatic heterocycles include pyridine, pyridazine, pyrimidine, pyrazine, furan, thiophene, pyrrole, oxazole, thiazole, isothiazole, imidazole, pyrazole, oxadiazole, triazole, thiadiazole and triazine groups. Examples of bicycles include in particular quinoline, isoquinoline and quinazoline groups (for two 6-membered rings) and indole, benzimidazole, benzoxazole, benzothiazole and indazole (for a 6-membered ring and a 5-membered ring). Nonaromatic heterocycles comprise in particular piperazine, piperidine, etc.

"Alkoxy" groups correspond to the alkyl groups defined hereinabove bonded to the molecule by an —O— (ether) bond. ($C_1$-$C_6$)alkoxy includes methoxy, ethoxy, propyloxy, butyloxy, pentyloxy, hexyloxy and the other isomeric forms thereof. ($C_1$-$C_3$)alkoxy includes methoxy, ethoxy, propyloxy, and isopropyloxy.

"Alcyl" groups correspond to the alkyl groups defined hereinabove bonded to the molecule by an —CO— (carbonyl) group. ($C_2$-$C_6$)acyl includes acetyl, propylacyl, butylacyl, pentylacyl, hexylacyl and the other isomeric forms thereof. ($C_2$-$C_3$)acyl includes acetyl, propylacyl and isopropylacyl.

"Alcohol" groups correspond to the alkyl groups defined hereinabove containing at least one hydroxyl group. Alcohol can be primary, secondary or tertiary. ($C_1$-$C_6$)alcohol includes methanol, ethanol, propanol, butanol, pentanol, hexanol and the other isomeric forms thereof. ($C_1$-$C_3$)alcohol includes methanol, ethanol, propanol and isopropanol.

"Ester" groups correspond to the alkyl groups defined hereinabove bonded to the molecule by an COO— (ester) bond. ($C_2$-$C_6$)ester includes methylester, ethylester, propylester, butylester, pentylester and the other isomeric forms thereof. ($C_2$-$C_3$)ester includes methylester and ethylester.

"Amine" groups correspond to the alkyl groups defined hereinabove bonded to the molecule by an —N-(amine) bond. ($C_1$-$C_6$)amine includes methylamine, ethylamine, propylamine, butylamine, pentylamine, hexylamine and the other isomeric forms thereof. ($C_1$-$C_3$)amine includes methylamine, ethylamine, and propylamine.

"Imine" groups correspond to the alkyl groups defined hereinabove having a (—C=N—) bond. ($C_1$-$C_6$)imine includes methylimine, ethylimine, propylimine, butylimine, pentylimine, hexylimine and the other isomeric forms thereof. ($C_1$-$C_3$)imine includes methylimine, ethylimine, and propylimine.

The halogen can be Cl, Br, I, or F, more preferably Br or F.

"Halogenoalkyl" groups correspond to the alkyl groups defined hereinabove having at least one halogen. The groups can be monohalogenated or polyhalogenated containing the same or different halogen atoms. For example, the group can be an trifluoroalkyl ($CF_3$—R). ($C_1$-$C_6$)halogenoalkyl includes halogenomethyl, halogenoethyl, halogenopropyl, halogenobutyl, halogenopentyl, halogenohexyl and the other isomeric forms thereof. ($C_1$-$C_3$)halogenoalkyl includes halogenomethyl, halogenoethyl, and halogenopropyl.

"Thioalkyl" groups correspond to the alkyl groups defined hereinabove bonded to the molecule by an —S-(thioether) bond. ($C_1$-$C_6$)thioalkyl includes thiomethyl, thioethyl, thiopropyl, thiobutyl, thiopentyl, thiohexyl and the other isomeric forms thereof. ($C_1$-$C_3$)thioalkyl includes thiomethyl, thioethyl, and thiopropyl.

"Sulfone" groups correspond to the alkyl groups defined hereinabove bonded to the molecule by an —SOO— (sulfone) bond. ($C_1$-$C_6$)sulfone includes methylsulfone, ethylsulfone, propylsulfone, butylsulfone, pentylsulfone, hexylsulfone and the other isomeric forms thereof. ($C_1$-$C_3$)sulfone includes methylsulfone, ethylsulfone and propylsulfone.

"Sulfoxyde" groups correspond to the alkyl groups defined hereinabove bonded to the molecule by an —SO— (sulfoxide) group. ($C_1$-$C_6$)sulfoxide includes methylsulfoxide, ethylsulfoxide, propylsulfoxide, butylsulfoxide, pentylsulfoxide, hexylsulfoxide and the other isomeric forms thereof. ($C_1$-$C_3$)sulfoxide includes methylsulfoxide, ethylsulfoxide, propylsulfoxide and isopropylsulfoxide.

"Heteroatom" denotes N, S, or O.

"Nucleoside" includes adenosine, thymine, uridine, cytidine and guanosine.

In a particular embodiment, the hydrocarbon group is a cycloalkylenyl such as a cyclopentadiene or a phenyl, or an heterocycle such as a furan, a pyrrole, a thiophene, a thiazole, an imidazole, a triazole, a pyridine, a pyrimidine, a pyrane, or a pyrazine. Preferably, the cycloalkylenyl or the heterocycle is selected from the group consisting of a cyclopentadiene, a pyrrole or an imidazole. In a preferred embodiment, the cycloalkylenyl or the heterocycle is substituted by an alcohol. Preferably, said alcohol is a ($C_1$-$C_3$)alcohol.

In an other embodiment, the hydrocarbon group is an alkylenyl with one or several double bonds. Preferably, the alkylenyl group has one double bond. Preferably, the alkylenyl group is a $(C_3-C_{10})$alkylenyl group, more preferably a $(C_4-C_7)$alkylenyl group. Preferably, said alkylenyl group is substituted by at least one functional group. More preferably, the functional group is selected from the group consisting of an hydroxy, an $(C_1-C_3)$alkoxy, an aldehyde, an $(C_2-C_3)$acyl, or an $(C_2-C_3)$ester. In a more preferred embodiment, the hydrocarbon group is butenyl substituted by a group —CH$_2$OH. Optionally, said alkenyl group can be the isoform trans (E) or cis (Z), more preferably a trans isoform (E). In a most preferred embodiment, the alkylenyl group is the (E)-4-hydroxy-3-methyl-2-butenyl. In an other preferred embodiment, the alkylenyl group is an isopentenyl, an dimethylallyl or an hydroxydimethylallyl.

In an additional embodiment, the hydrocarbon group is an alkyl group substituted by an acyl. More preferably, the hydrocarbon group is an $(C_4-C_7)$alkyl group substituted by an $(C_1-C_3)$acyl.

In a further preferred embodiment, R is selected from the group consisting of:

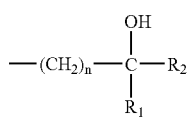

1)

wherein n is an integer from 2 to 20, $R_1$ is a $(C_1-C_3)$alkyl group, and $R_2$ is an halogenated $(C_1-C_3)$alkyl, a $(C_1-C_3)$alkoxy-$(C_1-C_3)$alkyl, an halogenated $(C_2-C_3)$acyl or a $(C_1-C_3)$alkoxy-$(C_2-C_3)$acyl. Preferably, $R_1$ is a methyl or ethyl group, and $R_2$ is an halogenated methyl (—CH$_2$—X, X being an halogen), an halogenated $(C_2-C_3)$acetyl, or $(C_1-C_3)$ alkoxy-acetyl. The halogenated methyl or acetyl can be mono-, di-, or tri-halogenated. Preferably, n is an integer from 2 to 10, or from 2 to 5. In a more preferred embodiment, n is 2. In a most preferred embodiment, n is 2, $R_1$ is a methyl and $R_2$ is an halogenated methyl, more preferably a monohalogenated methyl, still more preferably a bromide methyl. In a particularly preferred embodiment, n is 2, $R_1$ is a methyl, R2 is a methyl bromide. In a most preferred embodiment, R is 3-(bromomethyl)-3-butanol-1-yl.

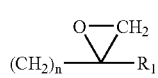

2)

wherein n is an integer from 2 to 20, and $R_1$ is a methyl or ethyl group. Preferably, n is an integer from 2 to 10, or from 2 to 5. In a more preferred embodiment, n is 2 and R1 is a methyl.

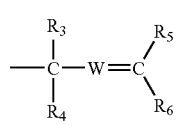

3)

wherein $R_3$, $R_4$, and $R_5$, identical or different, are a hydrogen or $(C_1-C_3)$alkyl group, W is —CH— or —N—, and $R_6$ is an $(C_2-C_3)$acyl, an aldehyde, an $(C_1-C_3)$alcohol, or an $(C_2-C_3)$ester. More preferably, $R_5$ is a methyl and $R_3$ and $R_4$ are a hydrogen. More preferably, $R_6$ is —CH$_2$—OH, —CHO, —CO—CH$_3$ or —CO—OCH$_3$. Still more preferably, $R_6$ is —CH$_2$—OH. More preferably, W is —CH—. Optionally, the double-bond between W and C is in conformation trans (E) or cis (Z). More preferably, the double-bond between W and C is in conformation trans (E).

The group Y can allow to design a prodrug. Therefore, Y is enzymolabile group which can be cleaved in particular regions of the subject. The group Y can also be targeting group. In a preferred embodiment, Y is O$^-$Cat+, a group -A-R, or a radical selected from the group consisting of a nucleoside, a monosaccharide, an epoxyde and a halohydrin. Preferably, Y is an enzymolabile group. Preferably, Y is O$^-$Cat+, a group -A-R, or a nucleoside. In a first preferred embodiment, Y is O$^-$Cat+. In a second preferred embodiment, Y is a nucleoside.

In a preferred embodiment, Cat$^+$ is H$^+$, Na$^+$, NH$_4^+$, K$^+$, Li$^+$, (CH$_3$CH$_2$)$_3$NH$^+$, lysine, or any other suitable pharmaceutically acceptable cation.

In a preferred embodiment, A is O, CHF, CF$_2$ or CH$_2$. More preferably, A is O or CH$_2$.

In a preferred embodiment, B is O or NH. More preferably, B is O.

In a preferred embodiment, m is 1 or 2. More preferably, m is 1.

In one particular embodiment, phosphoramidate esters according to the present invention comprise the compounds of formula (II):

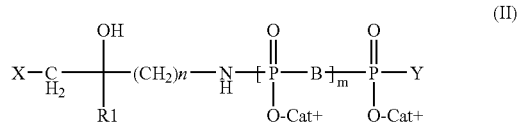

(II)

in which X is an halogen (preferably selected from I, Br and Cl), B is O or NH, m is an integer from 1 to 3, R1 is a methyl or ethyl group, Cat+ represents one (or several, identical or different) organic or mineral cation(s) (including the proton), and n is an integer from 2 to 20, and Y is O$^-$Cat+, a nucleoside, or a radical -A-R, wherein A is O, NH, CHF, CF$_2$ or CH$_2$ and R is selected from the group of 1), 2) or 3). Preferably, Y is O$^-$Cat+, or a nucleoside. More preferably, Y is O$^-$Cat+. Preferably, R1 is a methyl. Preferably, n is 2. Preferably, X is a bromide. Preferably, B is O. Preferably, m is 1 or 2. More preferably, m is 1.

For example, phosphoramidate esters according to the present invention comprise the compounds of formula (III):

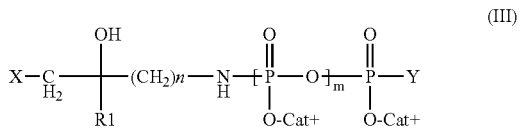

(III)

wherein X, R1, n, m and Y have the aforementioned meaning.

In one preferred embodiment, phosphoramidate esters according to the present invention comprise the compounds of formula (IV):

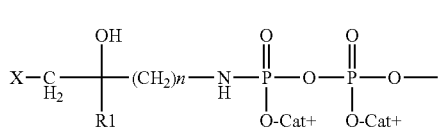
(IV)

in which X is an halogen (preferably selected from I, Br and Cl), R1 is a methyl or ethyl group, Cat+ represents one (or several, identical or different) organic or mineral cation(s) (including the proton), and n is an integer from 2 to 20. Preferably, R1 is a methyl. Preferably, n is 2. Preferably, X is a bromide.

In a most preferred embodiment, phosphoramidate esters according to the present invention comprise the compound of formula (V):

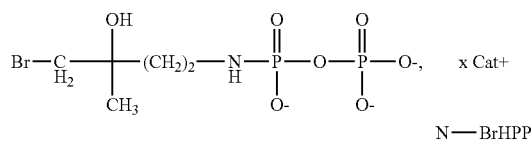
(V)

N—BrHPP

Preferably x Cat+ is 1 or 2 Na$^+$.

In one particular embodiment, phosphoramidate esters according to the present invention comprise the compounds of formula (VI):

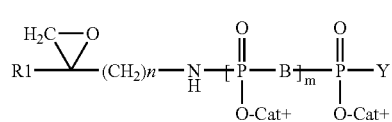
(VI)

in which R1 is a methyl or ethyl group, Cat+ represents one (or several, identical or different) organic or mineral cation(s) (including the proton), B is O or NH, m is an integer from 1 to 3, and n is an integer from 2 to 20, and Y is O$^-$Cat+, a nucleoside, or a radical -A-R, wherein A is O, NH, CHF, CF$_2$ or CH$_2$, and R is selected from the group of 1), 2) or 3). Preferably, Y is O$^-$Cat+, or a nucleoside. More preferably, Y is O$^-$Cat+. Preferably, R1 is a methyl. Preferably, n is 2. Preferably, B is O. Preferably, m is 1 or 2. More preferably, m is 1.

For example, phosphoramidate esters according to the present invention comprise the compounds of formula (VII):

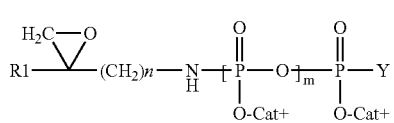
(VII)

wherein R1, n, m and Y have the above mentioned meaning.

In one preferred embodiment, phosphoramidate esters according to the present invention comprise the compounds of formula (VIII):

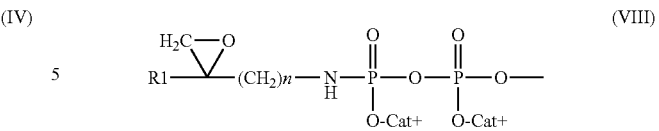
(VIII)

in which R1 is a methyl or ethyl group, Cat+ represents one (or several, identical or different) organic or mineral cation(s) (including the proton), and n is an integer from 2 to 20. Preferably, R1 is a methyl. Preferably, n is 2.

In a most preferred embodiment, phosphoramidate esters according to the present invention comprise the compound of formula (IX):

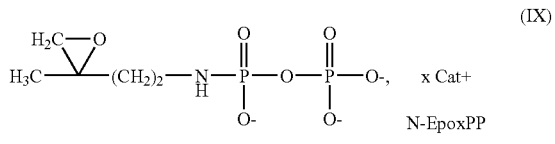
(IX)

N-EpoxPP

Preferably x Cat+ is 1 or 2 Na$^+$.

In one particular embodiment, phosphoramidate esters according to the present invention comprise the compounds of formula (X):

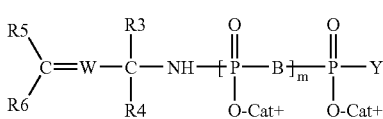
(X)

in which R$_3$, R$_4$, and R$_5$, identical or different, are a hydrogen or (C$_1$-C$_3$)alkyl group, W is —CH— or —N—, R$_6$ is an (C$_2$-C$_3$)acyl, an aldehyde, an (C$_1$-C$_3$)alcohol, or an (C$_2$-C$_3$) ester, Cat+ represents one (or several, identical or different) organic or mineral cation(s) (including the proton), B is O or NH, m is an integer from 1 to 3, and Y is O$^-$Cat+, a nucleoside, or a radical -A-R, wherein A is O, NH, CHF, CF$_2$ or CH$_2$, and R is selected from the group of 1), 2) or 3). Preferably, Y is O$^-$Cat+, or a nucleoside. More preferably, Y is O$^-$Cat+. More preferably, R$_3$ and R$_4$ are a hydrogen and R$_5$ is a methyl. More preferably, R$_6$ is —CH$_2$—OH, —CHO, CO—NH$_2$, —NH$_2$, or —CO—OCH$_3$. Still more preferably, R$_6$ is —CH$_2$—OH. More preferably, W is —H—. Preferably, B is O. Preferably, m is 1 or 2. More preferably, m is 1. Optionally, the double-bond between W and C is in conformation trans (E) or cis (Z). More preferably, the double-bond between W and C is in conformation trans (E).

For example, phosphoramidate esters according to the present invention comprise the compounds of formula (XI):

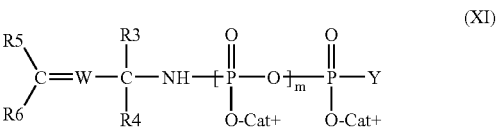
(XI)

wherein R3, R4, R5, R6, W, m, and Y have the above-mentioned meaning. Preferably, W is —CH— or —N—. Preferably, R3 and R4 are hydrogen. Preferably, R5 is a methyl. Preferably, R6 is —CH$_2$—OH.

In a most preferred embodiment, phosphoramidate esters according to the present invention comprise the compound of formula (XII):

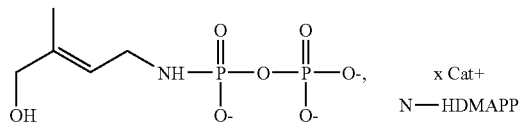

(XII)   x Cat+
N—HDMAPP

These compounds may be produced according to various techniques, for example using methods disclosed in PCT Publications nos. WO 00/12516, WO 00/12519, WO 03/050128, and WO 03/009855, the disclosures of which are incorporated herein by reference.

In a most preferred embodiment, the synthetic γδT lymphocyte activating compound is selected from the group consisting of N-HDMAPP, N-Epox-PP, and N-BrHPP, more preferably N-HDMAPP and N-BrBPP, still more preferably N-HDMAPP.

Phosphoramidate esters according to the present invention can be for example prepared by the following reactions (Reactions A, A(1), A(2), A(3), B, C or C(1).

Diphosphoramidate Monoesters Scheme: Reaction A

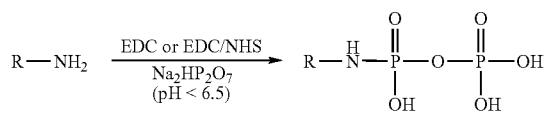

Diphosphoramidate Monoesters Alternative Scheme: Reaction A(1)

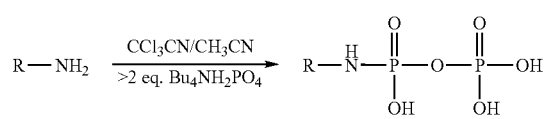

Diphosphoramidate monoesters according to the present invention can also be prepared using the following two reactions (Reactions A(2), A(3)). These synthetic schemes are preferred for larger scale preparations of diphosphoramidate monoesters and involve the formation of a monophosphoramidate monoester intermediate which is of interest for pharmaceutical development since it is considered as a potential metabolite or degradation product.

Diphosphoramidate Monoesters Alternative Scheme: Reaction A(2)

Reaction A(2) can be advantageously used when the starting alkyl precursor (R—NH$_2$) is not readily accessible, the starting molecule being preferably an alkylhalide R—X, with X=I, Br or Cl.

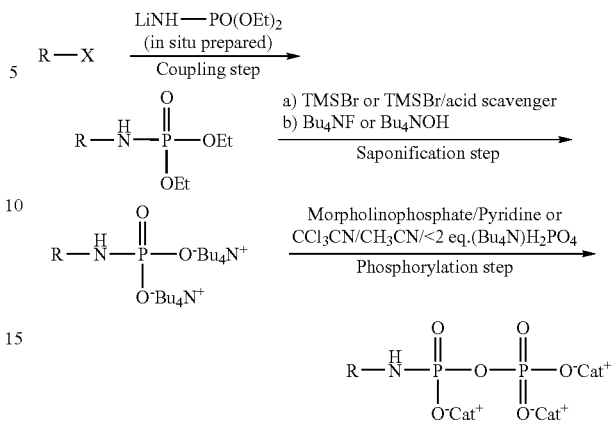

The coupling step of A(2) involves the in situ preparation of a lithium salt from deprotonation of the commercially available diethylphosphoramidate (NH$_2$—P(OEt)$_2$). This coupling step can be conducted following the procedure reported by Cox et al (2002), the disclosure of which is incorporated herein by reference.

The saponification step of reaction A(2) involves a two-step procedure leading to a complete removal of O-Ethyl esters functions. This reaction has to be performed preferably under neutral or basic conditions in order to prevent the hydrolysis of the phosphoramidate linkage (P—NH linkage). This reaction can be conducted with trimethylsilyl bromide (TMSBr) with subsequent removal of the resulting TMS-esters with tetrabutylammonium fluoride (Bu$_4$NF) as described in Valentijn et al (1991) or using TMSBr in the presence of Sym-collidine (acid scavenger) as described in Valentijn (1995) with subsequent basic hydrolysis of the resulting TMS-esters with tetrabutylammonium hydroxide (Bu$_4$NOH). The disclosures of the above references are incorporated herein by reference.

The phosphorylation step of reaction A(2) can be conducted in two ways:

(i) reaction of the monophosphoramidate intermediate with a morpholinophosphate reagent (tetrabutylammoniurn salt), whose preparation from the commercially available dimethylchlorophosphate is detailed below (Reaction A(2)(a)). This reaction can be conducted following the procedure of Valentijn et al. (1991) as applied for the synthesis of pyrophosphonate analogues; or (ii) reaction of the monophosphoramidate intermediate with trichloroacetonitrile (CCl$_3$CN) as coupling reagent and less than 2 equivalents of the commercially available tetrabutylammonium dihydrogen phosphate (Bu$_4$N)H$_2$PO$_4$.

Preparation of a Morpholinophosphate Reagent: Reaction A(2)(a)

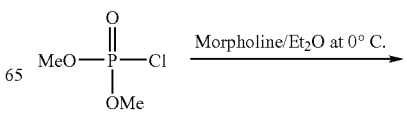

-continued

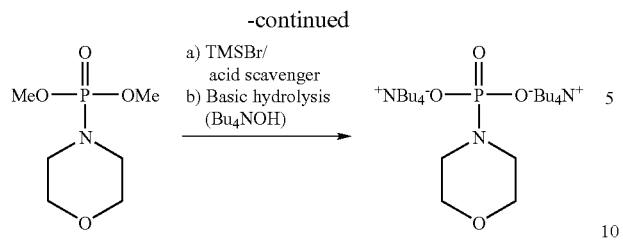

Diphosphoramidate Monoesters Alternative Scheme: Reaction A(3)

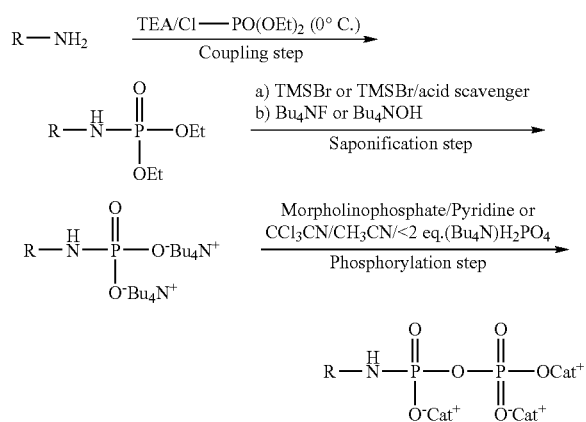

The coupling step of reaction A(3) involves the reaction of an alkylamine precursor with commercially available diethylchlorophosphate in the presence of triethylamine (TEA). This reaction can be conducted following the procedure described in Nikolaides et al, (Conversion of Amines to Phosphoesters: decyl diethyl phosphate, Organic Syntheses, CV 9, 194). Conditions for the saponification and phosphorylation steps are similar to those reported above (Reaction A(2)).

Depending on the type and reactivity of the functional groups provided by R, the person of skill in the art is able to adapt the synthesis examples presented herein, if necessary including the phases of protection/deprotection of the sensitive functional groups or those that can interact with the coupling reaction.

Imido-Diphosphoramidate Monoesters Scheme: Reaction B

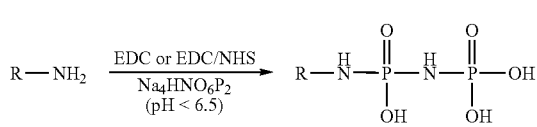

Triphosphoramidate Monoesters Scheme: Reaction C

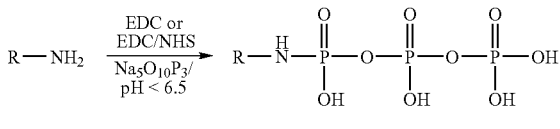

Triphosphoramidate Monoesters Alternative Scheme: Reaction C'

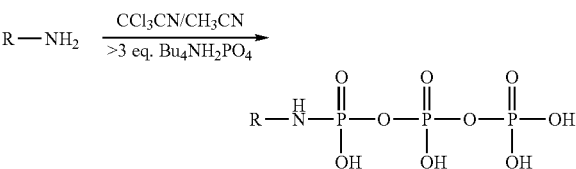

A, B and C reactions can be conducted as described in Sato et al (1990) and Chu et al (1983) using 1-Ethyl-3-(3-dimethylaminopropyl)-carbodiimide (EDC) as coupling reagent. Inorganic reagents $Na_2HP_2O_7$ (disodium pyrophosphate), $Na_4HNO_6P_2$ (tetrasodium imidodiphosphate) and $Na_5O_{10}P_3$ (pentasodium triphosphate) are commercially available. N-Hydroxysuccinimide (NHS) is often used to assist the carbodiimide coupling in the presence of EDC (Seghal & Vijay, 1994). The disclosures of the above references are incorporated herein by reference.

A, B and C reactions may also be performed in non-aqueous solvents with carbodimide reagents like DCC(N,N'-dicyclohexylcarbodiimide) using organic salts of di- or triphosphate. Carbodiimides have been widely employed in the synthesis of ortho- and pyrophosphate esters, nucleotides, cyclic phosphates, oligoribonucleotides, polynucleotides, nucleoside-5'-phosphoroamidates, and mixed anhydrides (Azzi et al., 1984), the disclosure of which is incorporated herein by reference.

Alternative reactions A(1) and C' can be conducted following the procedure described in Zhang & Poulter (1993), the disclosure of which is incorporated herein by reference, with trichloroacetonitrile ($CCl_3CN$) as coupling reagent. The inorganic reagent Tetrabutylammonium dihydrogen phosphate $(Bu_4N)H_2PO_4$ is commercially available.

The above reactions involve the protection of the sensitive functions of compound R—$NH_2$ or can react with the carbodiimide (EDC) or trichloroacetonitrile ($CCl_3CN$) reagents.

Phosphoramidate monoesters can be purified by preparative HPLC on C18 according to the method reported by Zhang & Poulter (1993). Or by preparative chromatography on silica gel using ammoniac isopropanol eluents according to the methods of International Patent publication no. WO 03/050128 filed 5 Dec. 2002. The disclosures of the above references are incorporated herein by reference.

Compounds comprising a nucleoside as Y group can be prepared, for example, by the following reactions. Depending on the type and reactivity of the functional groups provided by Y, the professional is able to adapt the following examples, if necessary including the phases of protection/deprotection of the sensitive functional groups or those that can interact with the coupling reaction.

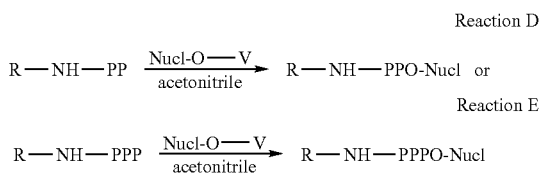

Reaction D

Reaction E where —O—V is a good leaving group beginning with V chosen, for example, from among tosyle, mesyle, triflyle, brosyle or bromium, PP represents the pyrophosphate group, PPP represents the triphosphate group, R— has the above mentioned meaning and Nucl is a nucleoside. Preferably, Nucl-O—V is selected from the group consisting of: 5'-O-Tosyladenosine, 5'-O-Tosyluridine, 5'-O-Tosylcytidine, 5'-O-Tosylthynidine or 5'-O-Tosyl-2'-deoxyadenosine.

For example, for the compound with R of group 1), the reaction procedure can be the following:

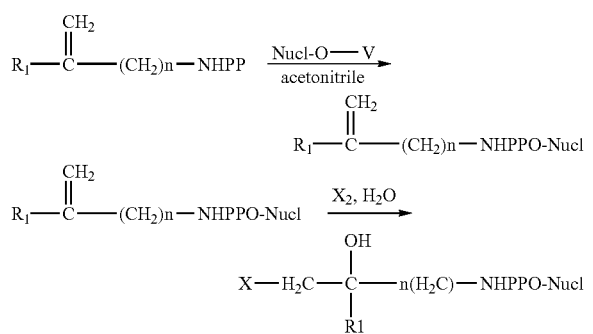

where —O—V is a good leaving group beginning with V chosen, for example, from among tosyle, mesyle, triflyle, brosyle or bromium, PP represents the pyrophosphate group and Nucl is a nucleoside. Preferably, Nucl-O—V is selected from the group consisting of: 5'-O-Tosyladenosine, 5'-O-Tosyluridine, 5'-O-Tosylcytidine, 5'-O-Tosylthymidine or 5'-O-Tosyl-2'-deoxyadenosine as described in Davisson et al, (1987), the disclosure of which is incorporated herein by reference.

The nucleophile substitution reaction can be carried out in conditions similar to those described by Davisson et al, (1987); and Davisson et al. (1986), the disclosures of which are incorporated herein by reference.

This reaction can also be used to prepare compound comprising a monosaccharide as group Y. In this case, Nucl-O—V is replaced by MonoSac-O—V, wherein Monosac is monosaccharide. For example, it is possible to use the MonoSac-O—Y group corresponding to compound Methyl-6-O-tosyl-alpha-D-galactopyranoside as described in publication Nilsson and Mosbach, (1980), incorporated herein by reference, or the commercially available mannose triflate compound.

This reaction can further be used to prepare compound comprising an oligosaccharide as group Y. In this case, Nucl-O—V is replaced by oligoSac-O—V, wherein oligoSac is an oligosaccharide. For example, it is possible to use the oligoSac-O—Y group corresponding to compound $6^4$-O-p-Toluenesulfonyl-β-cyclodextrin as described in publication (Organic syntheses, Vol. 77, p 225-228, the disclosure of which is incorporated herein by reference).

This reaction can be used to prepare compound comprising a polysaccharide as group Y. In this case, Nucl-O—V is replaced by polySac-O—V, wherein polySac is a polysaccharide. For example, it is possible to use the polySac-O—Y group corresponding to tosylated polysaccharide as described in publication Nilsson et al., (1981); and Nilsson and Mosbach, (1980), the disclosures of which are incorporated herein by reference. This coupling technique based on the activation of the hydroxyl groups of a polysaccharide support by tosylation allows for covalent coupling in an aqueous or an organic medium.

This reaction can also be used for preparing compound comprising an aldehyde derivative as group Y by choosing, instead of Nucl, a derivative including a protected aldehyde function in the form of an acetal or any other group protecting this function.

Alternatively, compounds comprising a nucleoside as Y group can be prepared by the following reaction:

Reaction F

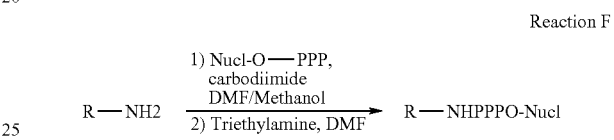

where PPP represents the triphosphate group, R— has the above mentioned meaning, DMF is dimethylformamide, and Nucl is a nucleoside. This reaction can be carried out in conditions similar to those described by Knorre et al. (1976), or by Bloom et al., U.S. Pat. No. 5,639,653 (1997), the disclosures of which are incorporated herein by reference, from alcohol and a nucleotide with formula Nucl-O—PPP.

For example, for the compound with R of group 1), the reaction procedure can be the following:

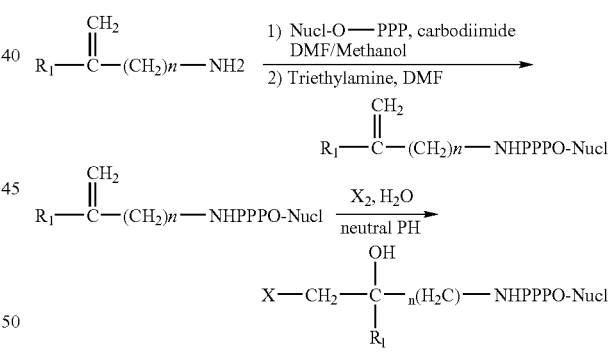

where PPP represents the triphosphate group, DMF is dimethylformamide, and Nucl is a nucleoside.

This reaction can also be applied to the preparation of oligonucleotides 5'-triphosphate ?-esters as indicated by the authors of publication Knorre et al. (1976).

Compounds comprising a nucleic acid as Y group, more particularly a ribonucleic acid, can be prepared in conditions similar to those described in publication F. Huang et al (1997). The authors describe a universal method from catalytic RNA that is applicable to any molecule comprising a free terminal phosphate group. Compounds structurally related to the phosphohalohydrin group such as isopentenyl pyrophosphate or thiamine pyrophosphate are used or mentioned by these authors (see p. 8968 of F. Huang et al (1997)). It should also be noted that the experimental conditions for the coupling procedure (in particular pH conditions) described in the section <<Reaction of Isolate 6 pppRNA with phosphate containing Nucleophiles >> on page 8965 are compatible with the presence of a halohydrine function.

Compounds comprising an amino acid, a peptide or a protein derivative as Y group can be obtained using the well known reactivity of their primary amine or thiol function on an epoxyde function ($S_N2$ reaction). This type of coupling classically involves an intermediate group still called "linker" bearing an epoxyde function. An example of a reaction procedure using this type of coupling is provided below.

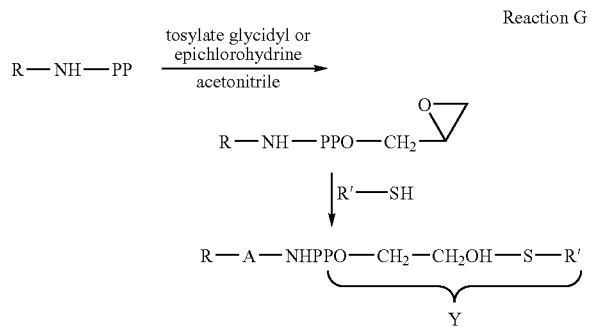

Reaction G where PP represents the pyrophosphate group, R— has the above mentioned meaning and R'—SH is an amino acid, a peptide or a protein derivative. The first phase can be carried out in conditions similar to those described by Davisson et al. (1987) and Davisson et al, (1986), the disclosures of which are incorporated herein by reference, from the tetrabutylammonium salt of the initial compound and commercially available compounds such as glycidyl tosylate or epichlorohydrine. This reaction can also be carried out with thriphosphate compounds. Alternatively, a primary amine R'—$NH_2$ can be used instead of R'—SH. Without the reaction with R'—SH, the first reaction can be used to prepare compound comprising an epoxyde derivative.

Alternatively, compounds comprising an amino acid, a peptide or a protein derivative as Y group can be prepared by the following reaction:

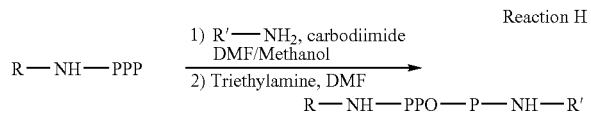

Reaction H where PPP represents the triphosphate group, PP represents the pyrophosphate group, P represents the phosphate group, R— has the above mentioned meaning and R'—NH is an amino acid, a peptide or a protein derivative. The reaction can be carried out in conditions similar to those described by Knorre et al. (1976), the disclosure of which is incorporated herein by reference, from compound (R—NH—PPP) and an amino acid, peptide or a protein with formula R'—$NH_2$. This reaction involves the protection of the sensitive functions of compound R'—$NH_2$ or can react with the carbodiimide (in particular, the carboxyl function).

Tri or tetra-n-butylammonium salts of phosphoric, pyrophosphoric, triphosphoric, tetra-phosphoric or polyphosphoric acid can be prepared from commercially available corresponding acids.

Derivatives with a related structure such as derivatives of methanetrisphosphonic acid described in publication Liu et al (1999), the disclosure of which is incorporated herein by reference, can also be prepared according to the reaction procedure.

The above mentioned reactions can be extrapolated to a very large spectrum of molecules or biomolecules by using the reactivity of the hydroxyl, amine, phosphate or thiol functions. Thereby, inositol derivatives can be prepared according to reactions D or E by activation of the hydroxyl function. Derivatives of folic acid (vitamin B9) or tetrahydrofolic acid can be prepared according to reactions G or H by calling on the reactivity of the primary amine function.

Of course, other types of coupling can be considered and the professional can have access to a large choice of reactions.

Thereby, coupling by phosphorylation of carboxylic acid or phenol groups can be used for the formation of fatty acid, lipid or certain flavonoid derivatives.

The phosphoramidate ester γδT lymphocyte activating compound can be a molecule produced ex vivo or in vitro. It may be a purified or otherwise artificially produced (e.g., by chemical synthesis, or by microbiological process) endogenous ligand, or a fragment or derivative thereof, or an antibody having substantially the same antigenic specificity. The phosphoramidate esters according to the present invention are preferably capable of selectively activating Vγ9Vδ2 T lymphocytes. Selective activation of Vγ9Vδ2 T lymphocytes indicates that the compound has a selective action towards specific cell populations, and essentially does not activate other T cell sub-types, such as Vδ1 T cells. Such selectivity, as disclosed in the present application, suggests that preferred compounds can cause a selective or targeted activation of the proliferation or biological activity of Vγ9Vδ2 T lymphocytes.

In a preferred aspect, the γδ T cell activator may increase the biological activity of γδ T cells, preferably increasing the activation of γδ T cells, particularly increasing cytokine secretion from γδ T cells or increasing the cytolytic activity of γδ T cells, with or without also stimulating the expansion of γδ T cells. In typical embodiments, a γδ T cell activator allows the cytokine secretion by γδ T cells to be increased at least 2, 3, 4, 10, 50, 100-fold, as determined in vitro.

Cytokine secretion and cytolytic activity can be assessed using any appropriate in vitro assay, or those provided in the examples herein. For example, cytokine secretion can be determined according to the methods described in Espinosa et al. (J. Biol. Chem., 2001, Vol. 276, Issue 21, 18337-18344), describing measurement of TNF-α release in a bioassay using TNF-α-sensitive cells. Briefly, $10^4$ γδT cells/well are incubated with stimulus plus 25 units of IL2/well in 100 μl of culture medium during 24 h at 37° C. Then, 50 μl of supernatant are added to 50 μl of WEHI cells plated at $3 \times 10^4$ cells/well in culture medium plus actinomycin D (2 μg/ml) and LiCl (40 mM) and incubated for 20 h at 37° C. Viability of the TNF-α-sensitive cells and measured with a 3-(4,5-dimethylthiazol-2-yl)-2,5-diphenyltetrazolium bromide assay. 50 μl of 3-(4,5-dimethylthiazol-2-yl)-2,5-diphenyltetrazolium bromide (Sigma; 2.5 mg/ml in phosphate-buffered saline) per well were added, and after 4 h of incubation at 37° C., 50 μl of solubilization buffer (20% SDS, 66% dimethyl formamide, pH 4.7) are added, and absorbance (570 nm) is measured. Levels of TNF-α release is then calculated from a standard curve obtained using purified human rTNF-α (PeproTech, Inc., Rocky Hill, N.J.). Interferon-γ released by activated T cells is measured by a sandwich enzyme-linked immunosorbent assay. $5\times10^4$ γδT cells/well are incubated with stimulus plus 25 units of IL2/well in 100 μl of culture medium during 24 h at 37° C. Then, 50 μl of supernatant are harvested for enzyme-linked immunosorbent assay using mouse monoclonal antibodies (BIOSOURCE, Camarillo, Calif.).

A preferred assay for cytolytic activity is a $^{51}$Cr release assay. In exemplary assays, the cytolytic activity of γδ T cells is measured against autologous normal and tumor target cell lines, or control sensitive target cell lines such as Daudi and control resistant target cell line such as Raji in 4 h $^{51}$Cr release assay. In a specific example, target cells were used in amounts of $2\times10^3$ cells/well and labeled with 100 μCi $^{51}$Cr for 60 minutes. Effector/Target (E/T) ratio ranged from 30:1 to 3.75:1. Specific lysis (expressed as percentage) is calculated using the standard formula [(experimental-spontaneous release/total-spontaneous release)×100].

Use of γδ T Lymphocyte Activators According to the Present Invention

The invention concerns a pharmaceutical composition comprising a γδ T cell activator according to the present invention. More particularly, said pharmaceutical composition comprises a therapeutically effective amount of γδ T cell activator, optionally together with a pharmaceutically acceptable carrier. Also encompassed by the invention is the use of a γδT activator according to the present invention for the manufacture of a pharmaceutical preparation, preferably for the treatment of a cancer, an infectious disease, an autoimmune disease or an allergic disease.

In one aspect, the invention discloses a method for regulating γδ T cells in a human subject, said method comprising the step of administering, in at least one treatment, a therapeutically effective amount of a γδ T cell activator according to the present invention, optionally together with a pharmaceutically acceptable carrier. More particularly, said method aims to stimulating γδ T cells in a human subject.

In a particular embodiment, the amount of said γδ T cell activator is sufficient to expand the γδ T cell population in a subject to reach at least 10%, 15%, 20%, 30%, 40%, 50% or 60%, or between 30-90% of total circulating lymphocytes. In another embodiment, the amount of said γδ T cell activator is sufficient to induce an at least 10-fold increase in the γδ T cell population in a subject. Preferably, said γδ T cell population is assessed between day 4 and day 8 following administration of said γδ T cell activator, more preferably at day 5, 6 or 7 following administration of said γδ T cell activator. Preferably, said γδ T cell population is assessed by flow cytometry. Preferably, said γδ T cells are Vγ9/Vδ2 T cells.

In a preferred embodiment, the invention concerns a method for treating a cancer, an infectious disease, an autoimmune disease or an allergic disease in a subject, said method comprising the step of administering, in at least one treatment, a therapeutically effective amount of a γδ T cell activator according to the present invention, optionally together with a pharmaceutically acceptable carrier.

In the above methods and uses, the subject is preferably a human subject, such as a subject having a cancer, an infectious disease, an autoimmune disease or an allergic disease. The invention is indeed suitable to treat all conditions caused by or associated with the presence of pathological cells which are sensitive to γδ T cell lysis.

The invention is particularly suited to stimulate the anti-tumor immunity of a subject having a solid or hematopoietic tumor. Preferably, said tumor is selected from the group consisting of lung, colorectal, prostate, breast or epidermoid head or neck tumors. In a preferred aspect of the invention, said tumor is a renal cancer, preferably a metastatic renal cancer. Alternatively, said tumor is selected from the group consisting of a melanoma, ovarian cancer, pancreas cancer, neuroblastoma, head or neck cancer, bladder cancer, renal cancer, brain cancer and gastric cancer. In preferred embodiments, the compounds can be used for the treatment of cancer as described in International Patent Application number PCT/IB2003/006375, filed Dec. 2, 2003, the disclosure of which is incorporated herein.

The invention is also suitable to stimulate an anti-viral immune response in a subject having an infection by a virus selected from HIV, CMV, EBV, Influenza virus, HCV, HBV, etc.

The compounds of the invention are also suitable in methods of stimulating an immune response in a subject having an infection by a pathogen causing tuberculosis, malaria, tularemia, colibacillosis, etc.

The compounds of the invention are also suitable in methods of treating (e.g., for stimulating an immune response in) a subject having an autoimmune disease, such as diabetes, multiple sclerosis, rheumatoid arthritis, etc. or a subject having an allergic disease, including asthma, airway hyper-responsiveness, etc. In preferred embodiments the compounds are used in therapeutic indications and according to the teachings of International Patent Application number WO2000US0026684 filed on 28 Sep. 2000 by Gelfand, Born, Lahn, and Kanehiro; International Patent Publication no. WO 00/00182, filed 24 Jun. 1999 by Jomaa; and U.S. Provisional patent application No. 60/564,959 filed Apr. 26, 2004 by Tiollier, the disclosures of each of the references incorporated herein by reference.

Preferably, dosage (single administration) of a phosphoramidate ester compound according to the present invention for treatment is between about 1 μg/kg and about 1.2 g/kg.

It will be appreciated that the above dosages related to a group of compounds, and that each particular compound may vary in optimal doses, as further described herein for exemplary compounds. Nevertheless, compounds are preferably administered in a dose sufficient to significantly increase the biological activity of γδ T cells or to significantly increase the γδ T cell population in a subject. Said dose is preferably administered to the human by intravenous (i.v.) administration during 2 to 180 min, preferably 2 to 120 min, more preferably during about 5 to about 60 min, or most preferably during about 30 min or during about 60 min.

In preferred exemplary compounds, a compound of formula II to XII is administered in a dosage (single administration) between about 1 μg/kg and about 1.2 g/kg, preferably between about 10 μg/kg and about 1.2 g/kg, more preferably between about 20 μg/kg and about 100 mg/kg. Most preferably, dosage (single administration) for three-weekly or four-weekly treatment (treatment every three weeks or every third week) is between about 1 μg/kg and about 1.2 g/kg, preferably between about 10 μg/kg and about 20 mg/kg, more preferably between about 10 μg/kg and about 100 mg/kg. This dose is preferably administered to the human by intravenous (i.v.) administration during 2 to 180 min, preferably 2 to 120 min, more preferably during about 5 to about 60 min, or most preferably during about 30 min or during about 60 min.

The active ingredients may be administered through different routes, typically by injection or oral administration. Injection may be carried out into various tissues, such as by intravenous, intra-peritoneal, intra-arterial, intramuscular, intra-dermic, subcutaneous, etc. Preferred administration routes for the activators are intravenous and intra-muscular.

Preferred administration routes for the cytokine are subcutaneous, intravenous and intra-muscular.

The invention provides a method of regulating the activity of γδ T cells in a mammalian subject, the method comprising administering to a subject in need thereof an effective amount of a γδ T cell activator according to a treatment cycle in which γδ T cell activity, preferably the γδ T cell rate (number of γδ T cells), is allowed to return to substantially basal rate prior to a second administration of the compound. As further described herein, in preferred embodiments, at least about one week, but more preferably at least about two weeks, are required for a patient's γδ T cell rate to return to substantially basal rate.

Cycles shorter than about 7 days do not permit suitable stimulation of γδ T cell activity. The course of a preferred cycle is an at least 1-weekly cycle, but more preferably at least a 2-weekly cycle (at least about 14 days), or more preferably at least 3-weekly or 4-weekly, though cycles anywhere between 2-weekly and 4-weekly are preferred. Also effective and contemplated are cycles of up to 8-weekly, for example 5-weekly, 6-weekly, 7-weekly or 8-weekly.

In one preferred embodiment, administration of the γδ T cell activator occurs on the first day of a 2-weekly to 4-weekly cycle (that is, an about 14 to 28 day weeks repeating cycle). In a preferred embodiment, the γδ T cell activator is administered only the first day of the 2-weekly to 4-weekly, or preferably 3 weekly, cycle.

As mentioned, a subject will preferably be treated for at least two cycles, or more preferably for at least three cycles. In other aspect, treatment may continue for a greater number of cycles, for example at least 4, 5, 6 or more cycles can be envisioned.

Optionally, a γδ T cell activators according to the present invention can also be used in combination with a cytokine. Preferably, said cytokine is the interleukin 2 (IL-2) (Proleukin™, Chiron, Emeryville Calif., USA) or any biologically active fragment, variant or analogue thereof, i.e., any fragment, variant or analogue capable of binding to an IL-2 receptor and of inducing activation of γδT cells in the method of this invention. Preferably, said γδT activator and interleukin-2 polypeptide are administered separately to the subject.

Therefore, the methods of the invention comprises further administering a cytokine. While the compounds of the invention may be used with or without further administration, in a preferred aspect a cytokine can be administered, wherein said cytokine is capable of increasing the expansion of a γδ T cell population treated with a γδ T cell activator compound, preferably wherein the cytokine is capable of inducing an expansion of a γδ T cell population which is greater than the expansion resulting from administration of the γδ T cell activator compound in the absence of said cytokine. A preferred cytokine is an interleukin-2 polypeptide.

A cytokine having γδ T cell proliferation inducing activity, most preferably the interleukin-2 polypeptide, is administered at low doses, typically over a period of time comprised between 1 and 10 days. The γδ T cell activator is preferably administered in a single dose, and typically at the beginning of a cycle. Preferably, the interleukin-2 polypeptide is administered at a daily dose comprised between 0.2 and 2 MU per day, even more preferably between 0.2 and 1.5 MU, further preferably between 0.2 and 1 MU. The daily dose of cytokine, preferably an interleukin-2 polypeptide, is administered as a single injection or in two injections.

In preferred aspects, a cytokine, most preferably IL-2, is administered daily for up to about 10 days, preferably for a period of between about 3 and 10 days, or most preferably for about 7 days. Preferably, the administration of the cytokine begins on the same day (e.g. within 24 hours of) as administration of the γδ T cell activator. For example, in one aspect the cytokine is administered each day, while in other aspects the cytokine need not be administered on each day. When the cytokine is administered for about 7 to about 14 days, a 4-weekly treatment cycle is preferred. When the first component is administered for about 4 days, a 3-weekly day treatment cycle is preferred. In preferred embodiments, the compounds can be used according to any of the methods described in International Patent Application number PCT/IB2003/006375, filed Dec. 2, 2003, the disclosure of which is incorporated herein by reference.

The above methods and treatments may be used alone or in combination with other active agents or treatments. For instance, for the treatment of tumors, the invention may be used in combination with other anti-tumor agents or treatments, such as chemotherapy, radiotherapy or gene therapy.

The invention also relates to a product comprising a γδ T cell activator according to the present invention and an interleukin-2 polypeptide, for separate use, for regulating the activity of γδ T cells in a mammalian subject.

The invention concerns a vaccinal composition comprising a γδ T cell activator according to the present invention. The invention also concerns the use of a γδ T cell activator according to the present invention as a vaccine adjuvant.

Accordingly, the present invention discloses methods and compositions for enhancing and/or augmenting the immune response against an antigen in a mammal, notably a human, involving the conjoint immunization of the mammal with (i) a composition comprising an antigen and (ii) an adjuvant comprising a phosphoramidate ester compound according to the present invention. Preferably said composition comprising an antigen comprises a killed, inactivated or attenuated pathogen, microorganism or parasite. In other aspect, said composition comprising an antigen preferably comprises an enriched or purified polypeptide, lipid, polysaccharide, glycoprotein, glycolipid or nucleic acid antigen. Preferably said composition comprises at least 1, 2, 3, 4, 5, 10 or 15 distinct antigens, for example at least 1, 2, 3, 4, 5, 10 or 15 distinct polypeptides, or nuclei acids encoding such polypeptides. In preferred embodiments, the compounds can be used as described in U.S. Provisional Patent Application No. 60/564,959, filed Apr. 26, 2004, the disclosure of which is incorporated herein by reference.

The adjuvant composition will comprise an effective amount of a phosphoramidate ester compound according to the present invention, said amount being an effective amount allowing the elicitation of a humoral response, elicitation of a cytotoxic T lymphocyte (CTL) response, or elicitation of both a humoral response and a CTL response of the adjuvant composition with respect to at least one antigen. Preferably the phosphoramidate ester compound according to the present invention, is present in an amount effective to produce a greater immunological effect in eliciting a humoral response, a cytotoxic T lymphocyte (CTL) response or both a humoral response and a CTL response when administered conjointly with an antigen than that immunological effect produced when said antigen is administered in the absence of the adjuvant.

The antigen component of the composition can be selected from virtually any antigen, antigenic determinant or hapten of medical or veterinary interest, and particularly for those antigens for which an increase in immunogenicity is desired.

Therefore, the present invention concerns the use of a phosphoramidate ester compound according to the present invention, more preferably N-HDMAPP or N-BrHPP, as a vaccine adjuvant. The present invention further concerns a vaccine composition comprising an antigen or a combination of antigens, and a phosphoramidate ester compound according to the present invention, more preferably N-HDMAPP or N-BrHPP. Preferably, said composition comprises a therapeutically effective amount of antigen and an immune response enhancing or immune response augmenting amount of the phosphoramidate ester γδ T cell activator. Preferably, said vaccine composition prevents a microbial infection. Said microbial infection is caused by a microbe selected from the group consisting of viruses, fungi, parasites, yeast, bacteria, and protozoa. In a particular embodiment, said vaccine composition is BCG vaccine composition. Alternatively, said vaccine composition prevents or is a treatment against a tumor.

The present invention further concerns a vaccine kit comprising a suitable container containing a vaccine composition according to the present invention, more particularly comprising an antigen or a combination of antigens, and a phosphoramidate ester compound according to the present invention, more preferably N-HDMAPP or N-BrHPP. Optionally, said vaccine can comprise two separate suitable containers, one containing the antigen or the combination of antigens and the other containing a phosphoramidate ester compound according to the present invention, more preferably N-HDMAPP or N-BrHPP. Optionally, said container can be a syringe. Alternatively, said vaccine kit comprises one or two containers and a syringe.

The present invention concerns a method of improving the potency of a vaccine in a subject, or of immunizing a subject against a disease, more particularly a microbial infection, comprising the steps of:
 administering to said subject a composition comprising an antigen or a combination of antigens; and,
 conjointly administering to said subject a phosphoramidate ester compound according to the present invention, more preferably N-HDMAPP or N-BrHPP, more particularly an immune response enhancing amount thereof. Preferably, the γδ T cell activator, when administered conjointly with a composition comprising an antigen, is administered in an amount sufficient to enhance an immune response over that observed with said composition comprising an antigen in the absence of the γδ T cell activator. Preferably said composition comprising an antigen comprises a killed, inactivated or attenuated pathogen, microorganism or parasite. In other aspect, said composition comprising an antigen preferably comprises an enriched or purified polypeptide, lipid, polysaccharide, glycoprotein, glycolipid or nucleic acid antigen.

The present invention also concerns a method of immunizing a subject against a disease, more particularly a microbial infection, in a subject comprising administering to said subject (i) a composition comprising an antigen, and (ii) a phosphoramidate ester compound according to the present invention, more preferably N-HDMAPP or N-BrHPP. Preferably the γδ T cell activator is administered in an immune response enhancing amount. Preferably the γδ T cell activator and the composition comprising an antigen are administered as a single vaccine composition in a therapeutically effective amount.

Preferably, said γδ T cell activator is together with a pharmaceutically acceptable carrier. In a first aspect, said administrations of said antigen or combination of antigens and said γδ T cell activator are simultaneously. In a second aspect, said administrations of said antigen or combination of antigens and said γδ T cell activator are sequentially. More particularly, said γδ T cell activator can be administered prior to, concurrently with or subsequent to administration of an antigen or a combination of antigens to a subject for immunization purposes. Preferably, said antigen or combination of antigens are microbial antigens, preferably, viral, bacterial, fungal, protozoan, yeast or parasite antigens. In a preferred embodiment, said antigen is a antigen of *Mycobacterium bovis*. Optionally, said antigen or combination of antigens is a tumoral antigen.

Further aspects and advantages of this invention will be disclosed in the following examples, which should be regarded as illustrative and not limiting the scope of this application.

EXAMPLES

Example 1

Production of (E)-4-hydroxy-3-methylbut-2-enyl pyrophosphoramidate N-HDMAPP)

Preparation of (E)-4-Chloro-2-methylbut-2-en-1-ol 16 ml (179 mmol) of $TiCl_4$ was added under nitrogen to 360 ml of $CH_2Cl_2$. The solution was cooled to 90° C. and a solution of 10.0 g (119 mmol) of 2-methyl-2-vinyloxirane in 50 ml of $CH_2Cl_2$ was added drop wise keeping the temperature below −80° C. The red solution was then stirred at 80° C. for 2 hours and quenched with 600 ml of 1M HCl. The organic phase was separated and the aqueous phase was extracted with 3×500 ml of $Et_2O$. The combined organic phases were dried over $MgSO_4$, filtered and evaporated at 350 mbar at 25° C. to give 12.02 g (99.7 mmol, 84% yield) of 4-Chloro-2-methylbut-2-en-1-ol as brownish oil. The crude product was directly used in the next step.

Preparation of (E)-2-(4-Chloro-2-methylbut-2-en yloxy)tetrahydro-2H-pyran

To a solution of 11.5 g (95.37 mmol) of 4-Chloro-2-methylbut-2-en-1-ol in 120 ml of $CH_2Cl_2$ was added 26 ml (286.11 mmol) of Dihydropyrane (DHP). The solution was cooled at 0° C. and 2.4 g (9.53 mmol) of pyridinium p-toluene sulfonate (PPTS) was added portion wise. The solution was stirred for 3 hours at 0° C. The organic phase washed with 3×50 ml of water, dried over $Na_2SO_4$, filtered and concentrated to give the crude product. The product was then purified by chromatography on silica gel using heptane/EtOAc (9/1) as eluent. 12.35 g (60.33 mmol, 64% yield) of the protected allylic alcohol were isolated as colorless oil.

Preparation of (E)-2-(4-azido-2-methylbut-2-en yloxy)tetrahydro-2H-pyran

A solution of 11.43 g (175.86 mmol) of sodium azide ($NaN_3$) and 2.20 g (6.45 mmol) of tetrabutylammonium hydrogenosulfate in 60 ml of water was added to a solution of 12.0 g (58.62 mmol) of (E)-2-(4-Chloro-2-methylbut-2-en yloxy)tetrahydro-2H-pyran in 300 ml of pentane. The reaction mixture was stirred at room temperature overnight. The organic phase was separated and the aqueous phase was extracted with 3×150 ml of $Et_2O$. The combined organic phases were washed with brine, dried over $Na_2SO_4$, filtered and concentrated to give 11.21 g (53.06 mmol, 90% yield) of a mixture of azides isomers. No purification was done as infeasible separation was observed on silica gel. The product was used without further purification for the next step.

Preparation of (E)-3-methyl-4-(tetrahydro-2H-pyran-2-yloxy)but-2-en-1-amine 26 g (98.8 mmol) of triphenyl phosphine ($PPh_3$) were added to a solution of 11.0 g (52.07 mmol) of the crude azide obtained at the previous step and 18 ml of water in 180 ml of THF. The solution was stirred at room temperature overnight and the solvent was evaporated. The resulting crude product was purified by chromatography on silica gel (eluent: $CH_2Cl_2$/MeOH/$Et_3N$ 9/1/0.5) to give 6.47 g (34.91 mmol, 67% yield) of purified allylic amine obtained as a yellow oil. The isomeric ratio (E:Z) in the purified product was approx. 90:10 on the basis of $^1H$-NMR analysis.

Preparation of (E)-3-methyl-4-(tetrahydro-2H-pyran-2-yloxy)but-2-enyl pyrophosphoramidate Disodium pyrophosphate (0.25 mmol-1 eq.) and (E)-3-methyl-4-(tetrahydro-2H-pyran-2-yloxy)but-2-en-1-amine (46 mg-0.25 mmol-1 eq.) were dissolved in 3 ml of a 1/1 (v/v)

deionized water/acetonitrile mixture and introduced into in a glass reaction vessel. 12.5 ml of a 0.2 M deionized water/acetonitrile solution of 1-ethyl-3-(3-dimethylaminopropyl) carbodiimide hydrochloride (2.5 mmol-10 eq) were added dropwise using a syringe, while stirring at room temperature. The progress of the reaction was then monitored by Ionic Chromatography (HPAEC). After approx. 3 hours the reaction mixture was concentrated to a final volume of approx. 5 ml under reduced pressure and the crude material obtained at this stage was converted to the ammonium form by passing the aqueous solution through a column containing an excess of DOWEX 50WX8-200 ($NH_4^+$ form) resin eluted by two column volumes of deionized water. This treatment also allowed to remove unreacted carbodiimide and cationic by-products from the reaction medium. The collected solution was then concentrated to a final volume of approx. 5 ml by evaporation of water under reduced pressure (20 mbar-40° C.) and used directly for the next step.

For the purpose of performing biological testing, neutral aqueous solutions of the product was sterilized by filtration through 0.2 μm filter and stored at −20° C. In the case of testing performed in vivo the solutions are passed beforehand through a DOWEX 50WX8-200 cationic resin column ($Na^+$ form) eluted by two column volumes of deionized water.

The synthesis of (E)-4-hydroxy-3-methylbut-2-enyl pyrophosphoramidate (N-HDMAPP) was carried out according to the scheme below. For each step of this synthetic scheme the following references may be used for further guidance: Step 1: Hecht et al., *Tetrahedron Letters*, 43 (2002) 8929-8933; Step 2: Miyashita et al, *J. Org. Chem.*, 42 (1977) 3772-3774, Solladié et al, *J. Org. Chem.* 1993, 58, 2181-2185, and Marshall et al, *J. Org. Chem.* 1985, 50(10), 1602-1606; Step 3: Deslongchamps et al, *Can. J. Chem.* 1979, 57, 3262-3271; Step 4: Coperet et al, *Tetrahedron* 1996, 52 (35) 11520-11544; Step 5: Sato et al, *Chem. Phar. Bull*, 38(8), 2287-2289 (1990); and Step 6: Miyashita et al, *J. Org. Chem.*, 42 (1977) 3772-3774 (deprotection reaction only).

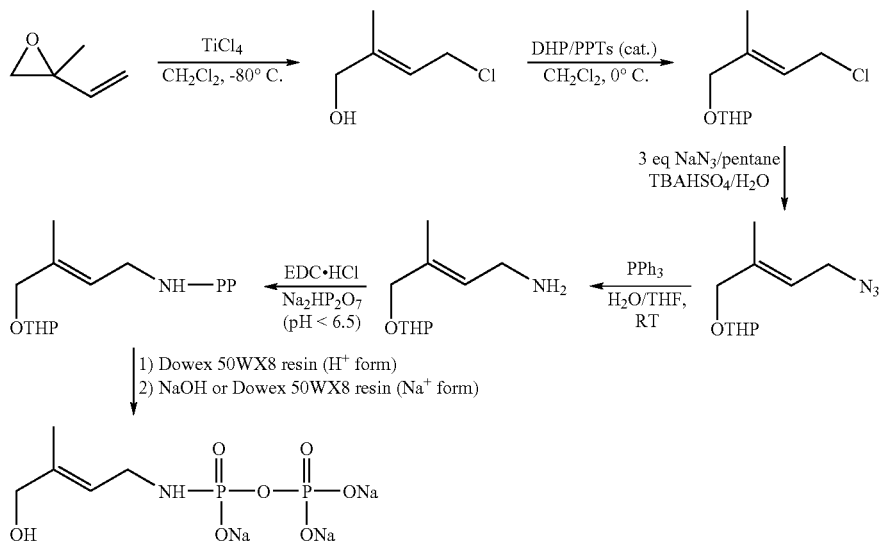

Preparation of (E)-4-hydroxy-3-methylbut-2-enyl pyrophosphoramidate (N-HDMAPP)

Complete removal of the of the protective tetrahydropyranyl (THP) group was achieved by passing the crude solution obtained at the previous step through a column containing (10 g-24 meq) of DOWEX 50 WX8-200 ($H^+$ form) resin eluted with two column volumes of deionized water. The resulting acidic solution was collected in a 50 ml-Falcon® tube placed in an ice bath. The resulting solution was immediately neutralized to pH 8 with 10% ammonium hydroxide solution. The product was then purified by anion exchange chromatography through a 5 g Sep-Pak Accell Plus QMA (Waters®) cartridge eluted in succession respectively by 5 mM, 10 mM, 25 mM, 50 mM, 75 mM, 100 mM and 200 mM aqueous hydrogenocarbonate solutions, with the eluted fractions being monitored by Ionic Chromatography (HPAEC). The fractions corresponding to the purified product were then combined and freeze-dried in order to remove ammonium hydrogenocarbonate. The isomeric ratio (E:Z) in the purified product was 87:13 on the basis of HPAEC analysis.

Pure (E)-4-hydroxy-3-methylbut-2-enyl pyrophosphoramidate was obtained by chromatographic purification (HPAEC) through IonPac® AS11 column, with multiple chromatographic passes being combined.

Example 2

Production of 3-methylbut-3-enyl pyrophosphoramidate (N-IPP)

Preparation of 3-methyl-3-buten-1,1-tosylate

Tosyl chloride (4.8 g, 25 mmol) and 4-(N,N-dimethylamino-)pyridine (3.4 g, 27.5 mmol) were mixed under magnetic stirring with 90 ml of anhydrous dichloromethane in a 250-ml three-necked flask cooled in an ice bath. A solution of 3-methyl-3-buten-1-ol (2.2 g, 25 mmol) in about 10 ml of anhydrous dichloromethane was then slowly introduced with a syringe through a septum in the flask, and the ice bath was then removed. The reaction was monitored by silica gel TLC (pentane/ethyl acetate, 85:15 (v/v)). After 2 h with constant stirring, the mixture was precipitated by dilution into 1 liter of hexane and filtered, and the filtrate was concentrated under reduced pressure. This filtration/suspension step was repeated using diethyl ether, and the resulting oil was purified by liquid chromatography on silica gel (pentane/ethyl acetate, 85:15 (v/v)), yielding a yellow oil of 3-methyl-3-buten-1-yl-tosylate (5.6 g, 23.5 mmol, 94% yield) kept under dry $N_2$ at 4° C.

Preparation of 4-azido-2-methyl-1-ene

To a solution of 2.0 g (8.32 mmol) of 3-methyl-3-buten-1-yl-tosylate in 20 ml of DMSO was added 820 mg (12.48 mmol) of sodium azide ($NaN_3$) and 125 mg (catalytic amount) of NaI. The reaction mixture was stirred at 55° C. overnight. The reaction mixture was cooled to room temperature and 120 ml of water was added. The solution was extracted with 3×100 ml of $Et_2O$. The combined organic phases were washed with 100 ml of water, 100 ml of brine, dried over $Na_2SO_4$, filtered and concentrated at 300 mmHg at room temperature. 875 mg (7.87 mmol, 95% yield) of 4-azido-2-methyl-1-ene were isolated as a brown oil.

Preparation of 3-methyl-3-en-1-amine

A solution of 500 mg (4.50 mmol) of 4-azido-2-methyl-1-ene, 3.92 g (14.95 mmol) of triphenyl phosphine $PPh_3$ and 2.7 ml of water in 27 ml of THF was stirred at room temperature overnight and the solvent was evaporated. The resulting crude product was then purified by chromatography on silica gel using $CH_2Cl_2$/MeOH/$Et_3N$ 9/1/0.5) as eluent. 125 mg (1.47 mmol) of 3-methyl-3-en-1-amine were isolated as yellow oil in 32% isolated yield. The purified amine was kept under dry $N_2$ and stored at −20° C. for the next step.

perature. The pH is eventually adjusted and maintained in the range 6-6.5 with addition of 0.1 N aqueous HCl. The progress of the reaction is then monitored by Ionic Chromatography (HPAEC). After approx. 3 hours the reaction mixture is concentrated to a final volume of approx. 5 ml under reduced pressure and the crude material obtained at this stage is converted to the ammonium form by passing the aqueous solution through a column containing an excess of DOWEX 50WX8-200 ($NH_4^+$ form) resin eluted by two column volumes of deionized water.

Purification of the crude solution is achieved by anion exchange chromatography through a Sep-Pak Accell Plus QMA (Waters®) cartridge following the procedure reported in Example 1 for the preparation of N-HDMAPP.

The synthesis of N-IPP, 5-bromo-4-hydroxy-4-methylpentyl pyrophosphoramidate (N-BrHPP) (Example 3) and N-EpoxPP (Example 4) are carried out according to the scheme below. For each step of this synthetic scheme the following references may be used for further guidance: Step 1: Davisson et al., *J. Org. Chem.*, 1986, 51, p 4768-4779; Step 2: Grieco et al, *Tetrahedron* 1986, 42 (11), 2847-2853, and Sahasrabudhe, K. et al., *J. Am. Chem. Soc.* 2003; 125(26); 7914-7922; Step 3: Brettle R. et al., *Bioorg. Med. Chem. Lett.*, vol. 6, p 291 (1996); Step 4: Sato et al, *Chem. Pharm. Bull*, 38(8), 2287-2289 (1990); Step 5: Espinosa, et al, (2001a) J Biol Chem 276, 18337-18344; and Step 6: International Patent publication no. WO 00/012519.

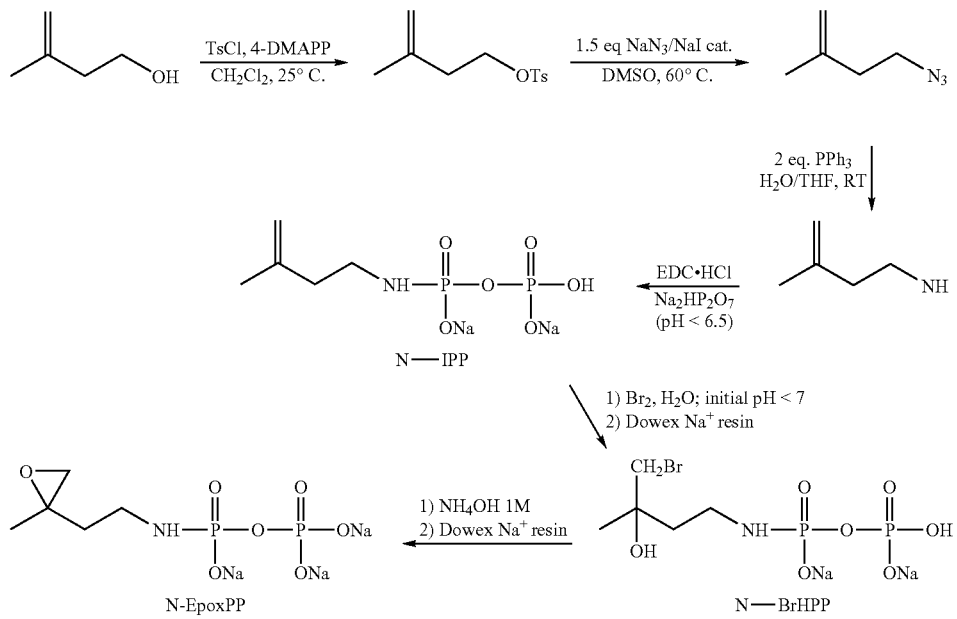

Preparation of 3-methylbut-3-enyl pyrophosphoramidate (N-IPP)

3-methylbut-3-enyl pyrophosphoramidate is prepared following the procedure reported in example 1 for the preparation of 3-methyl-4-(tetrahydro-2H-pyran-2-yloxy)but-2-enyl pyrophosphoramidate:

Disodium pyrophosphate (0.25 mmol-1 eq.) and 3-methyl-3-en-1-amine (0.25 mmol-1 eq.) are dissolved in 3 ml of a 1/1 (v/v) deionized water/acetonitrile mixture and introduced into in a glass reaction vessel. 12.5 ml of a 0.2 M deionized water/acetonitrile solution of 1-ethyl-3-(3 dimethylaminopropyl)carbodiimide hydrochloride (2.5 mmol-10 eq) are added dropwise using a syringe, while stirring at room tem- Example 3

Production of 5-bromo-4-hydroxy-4-methylpentyl pyrophosphoramidate (N-BrHPP)

As illustrated in the synthesis scheme below, the compound N-BrHPP can be prepared starting from the compound N-IPP described in Example 2 by addition of bromine water to the alkene function followed by a neutralization on DOWEX 50WX8-200 ($Na^+$ form) resin. The formation of the bromohydrin function with subsequent purification of the crude product can be conducted according to the experimental protocol provided in WO 00/012516 for the preparation of 3-(bromomethyl)-3-butanol-1-yl disphosphate. (BrBPP) or as described in Espinosa et al, *J Biol Chem*, 276, (2001) 18337-18344.

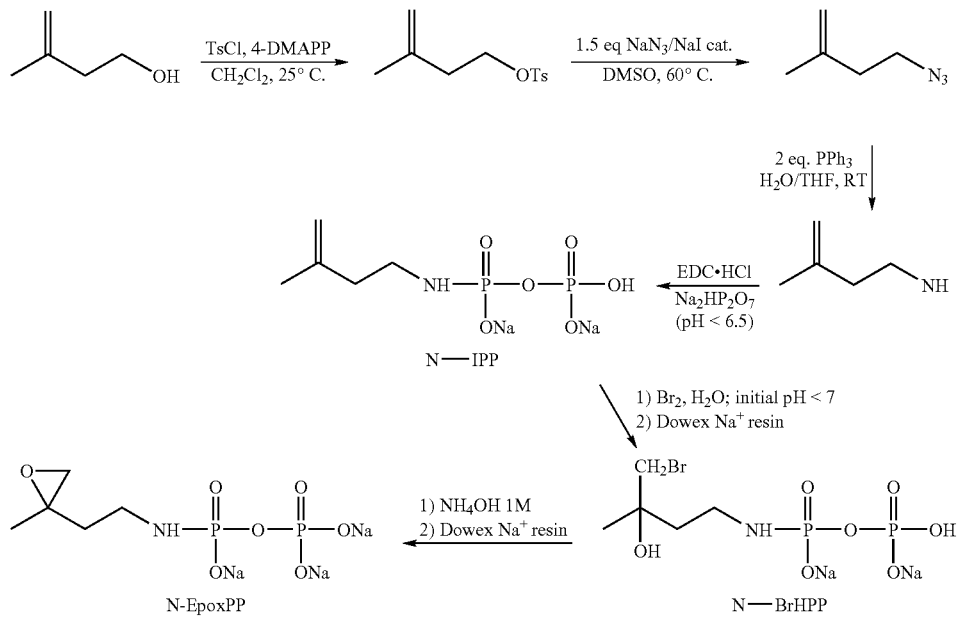

Example 4

Production of 2-(2-methyloxiran-2-yl)ethyl pyrophosphoramidate (N-EpoxPP)

As illustrated in the synthesis scheme below, the compound N-EpoxPP can be prepared starting from the compound N-BrHPP described in Example 3 by treatment with 1M ammonium hydroxide solution (epoxidation reaction) followed by a cationic exchange step on DOWEX 50WX8-200 (Na$^+$ form) resin. The epoxidation reaction with subsequent purification of the crude product can be conducted according to the experimental protocol provided in WO 00/012519 for the preparation of 3,4-epoxy-3-methyl-1-butyl-diphosphate (EpoxPP).

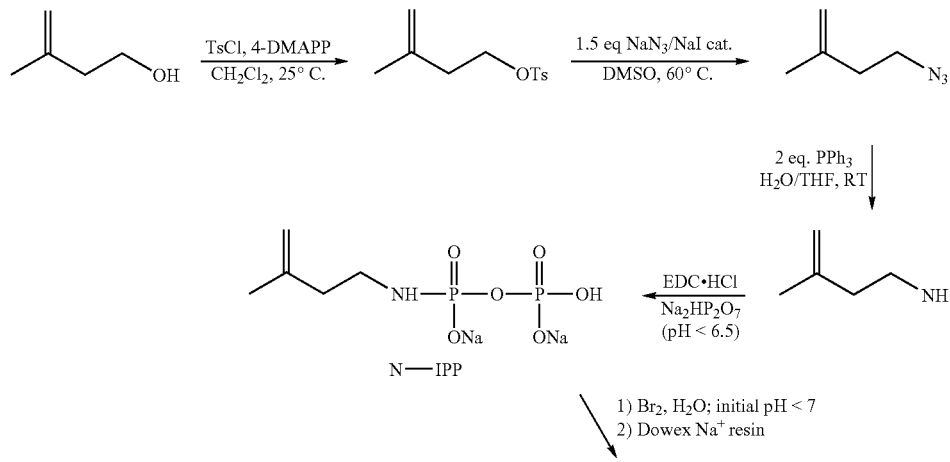

-continued

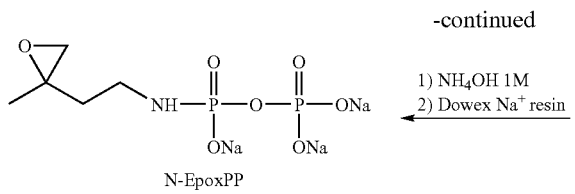
N-EpoxPP

1) NH$_4$OH 1M
2) Dowex Na$^+$ resin

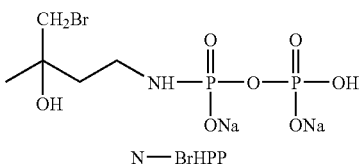
N—BrHPP

Example 5

In Vitro and In Vivo Dosage Response for N-HDMAPP Compound

Cytokine Release Assay

Cells (primary polyclonal human Vγ9Vδ2 T cells which have been expanded in vitro and stored frozen at day 12-15 of expansion) are thawed and rinsed twice and centrifuged. Upon elimination of supernatant and resuspension of cells, the cells are incubated for 24 h at 37° C. in the presence of IL2 100 IU/ml (final concentration). The cells are washed and centrifuged, following which the supernatant is eliminated and the cells are resuspended and adjusted to the adequate final concentration. The cells are added to the wells of a 96-well plate.

To one row of wells is added a standard dilution series of 3-(bromomethyl)-3-butanol-1-yl-diphosphate (BrHPP). Compounds to be tested, in this case (E)-4-hydroxy-3-methyl-2-butenyl pyrophosphate (HDMAPP) and the N-HDMAPP compound of the invention are added to experimental wells, after several dilutions.

Full plates are incubated 24 hours at 37° C. for stimulation of the γδ cells with the test compound and reference compounds, in this case N-HDMAPP, BrHPP and HDMAPP, as further described below. After this time, 100 μl of culture supernatant is taken for TNFα dosage. Measurement of the released TNFα dosage is performed as described by the manufacturer's instruction in the TNFα enzyme immunoassay kit (ref. 11121, Immunotech—Beckman Coulter). OD at 405 nm is read, the OD being proportional to the concentration of released TNFα in the culture supernatant. The data are processed with the Excel software to compare concentration of test compound versus concentration of TNFα and for the calculation of the EC50 for each test compound.

N-HDMAPP In Vitro Bioactivity

The bioactivity of the compound N-HDMAPP was assessed using a TNFα release assay as described above. In vitro activity is shown in FIG. 1. Compounds BrHPP and HDMAPP were included for purpose of comparison. The in vitro EC50 was then assessed in this in vitro relative screening test, where prior assays with calibrated cells using a BrHPP-standard composition presented an EC50 of about 15 nM for BrHPP. As will be appreciated, any other suitable assays such as cell amplification may be used in assessing compounds. The EC50 for N-HDMAPP was determined to be 0.63 nM while the in vitro EC50 for HDMAPP was 2.1 nM and the in vitro EC50 for BrHPP was 37.7 nM. Since the assay provides a relative result rather than absolute EC50 value, the results indicate that the N-HDMAPP compound has 3-4 times greater potency that the most potent compounds tested so far.

The maximum level of TNFα release was also assessed. As shown in FIG. 1, the N-HDMAPP compound brought about a maximum TNFα release greater than that with other compounds tested. While other compounds tested differed in potency (EC50), they showed similar maximum TNFα release levels—between about 1200 and 1500 pg/ml TNFα release. The N-HDMAPP compound, however, produced a statistically significant increase in maximum TNFα release of over about 1800 pg/ml TNFα release, suggesting that N-HDMAPP may lead to greater absolute Vγ9Vδ2 T cell activation in vivo that can be obtained at any concentration of other compounds.

REFERENCES

All the cited references are incorporated herein by reference.

Azzi, A., Casey, R. P. & Nalecz, M. (1984) The effect of N,N'-dicyclohexylcarbodiimide on enzymes of bioenergetic relevance. *Biochim. Biophys. Acta,* 768(3-4):209-226

Bank, I., Book, M., Huszar, M., Baram, Y., Schnirer, I., and Brenner, H. (1993). V delta 2+ gamma delta T lymphocytes are cytotoxic to the MCF 7 breast carcinoma cell line and can be detected among the T cells that infiltrate breast tumors. Clin Immunol Immunopathol 67, 17-24.

Behr, C., Poupot, R., Peyrat, M. A., Poquet, Y., Constant, P., Dubois, P., Bonneville, M., and Fournie, J. J. (1996). *Plasmodium falciparum* stimuli for human gammadelta T cells are related to phosphorylated antigens of mycobacteria. Infect Immun 64, 2892-2896.

Belmant, C., Espinosa, E., Halary, F., Tang, Y., Peyrat, M. A., Sicard, H., Kozikowski, A., Buelow, R., Poupot, R., Bonneville, M., and Fournie, J. J. (2000). A chemical basis for selective recognition of nonpeptide antigens by human delta T cells. Faseb J 14, 1669-1670.

Bukowski, J. F., Morita, C. T., Tanaka, Y., Bloom, B. R., Brenner, M. B., and Band, H. (1995). V gamma 2V delta 2 TCR-dependent recognition of non-peptide antigens and Daudi cells analyzed by TCR gene transfer. J Immunol 154, 998-1006.

Choudhary, A., Davodeau, F., Moreau, A., Peyrat, M. A., Bonneville, M., and Jotereau, F. (1995). Selective lysis of autologous tumor cells by recurrent gamma delta tumor-infiltrating lymphocytes from renal carcinoma. J Immunol 154, 3932-3940.

Chu, B. C. F., Wahl, G. M. and Orgel, L. E/, *Nucleid Acids Research, Vol* 11, No 18 (1983).

Constant, P., Poquet, Y., Peyrat, M. A., Davodeau, F., Bonneville, M., and Fournie, J. J. (1995). The antituberculous *Mycobacterium bovis* BCG vaccine is an attenuated mycobacterial producer of phosphorylated nonpeptidic antigens for human gamma delta T cells. Infect Immun 63, 4628-4633.

R. J. Cox, J. S. Gibson, M. B. Mayo Martin, *Chem BioChem,* 2002, 3, 874-886

Davisson et al., J. Org. Chem., 1987, 52, p 1794-1801.

Davisson et al., J. Org. Chem., 1986, 51, p 4768-4779.

Sato, E., Yoshikawa, M., and Kanaoka Y., *Chem. Pharm. Bull,* 38(8), 2287-2289 (1990).

Espinosa, E., Belmant, C., Pont, F., Luciani, B., Poupot, R., Romagne, F., Brailly, H., Bonneville, M., and Fournie, J. J. (2001a). Chemical synthesis and biological activity of bromohydrin pyrophosphate, a potent stimulator of human gamma delta T cells. J Biol Chem 276, 18337-18344.

Espinosa, E., Belmant, C., Sicard, H., Poupot, R., Bonneville, M., and Fournie, J. J. (2001b). Y2K+1 state-of-the-art on non-peptide phosphoantigens, a novel category of immunostimulatory molecules. Microbes Infect 3, 645-654.

Ferrarini, M., Heltai, S., Pupa, S. M., Mernard, S., and Zocchi, R. (1996). Killing of laminin receptor-positive human lung cancers by tumor infiltrating lymphocytes bearing gammadelta(+) t-cell receptors. J Natl Cancer Inst 88, 436-441.

Feurle, J., Espinosa, E., Eckstein, S., Pont, F., Kunzmann, V., Fournie, J. J., Herderich, M., and Wilhelm, M. (2002). *Escherichia coli* produces phosphoantigens activating human gamma delta T cells. J Biol Chem 277, 148-154.

Fisch, P., Moris, A., Rammensee, H. G., and Handgretinger, R. (2000). Inhibitory MHC class I receptors on gammadelta T cells in tumour immunity and autoimmunity. Immunol Today 21, 187-191.

Fournie, J. J., and Bonneville, M. (1996). Stimulation of gamma delta T cells by phosphoantigens. Res Immunol, 66th Forum in Immunology, 147, 338-347.

Fujimiya, Y., Suzuki, Y., Katakura, R., Miyagi, T., Yamaguchi, T., Yoshimoto, T., and Ebina, T. (1997). In vitro interleukin 12 activation of peripheral blood CD3(+)CD56(+) and CD3(+)CD56(−) gammadelta T cells from glioblastoma patients. Clin Cancer Res 3, 633-643.

Gober, H. J., Kistowska, M., Angman, L., Jeno, P., Mori, L., and De Libero, G. (2003). Human T cell receptor gammadelta cells recognize endogenous mevalonate metabolites in tumor cells. J Exp Med 197, 163-168.

Hayday, A. C. (2000). [gamma][delta] cells: a right time and a right place for a conserved third way of protection. Annu Rev Immunol 18, 975-1026.

Jomaa, H., Feurle, J., Luhs, K., Kunzmann, V., Tony, H. P., Herderich, M., and Wilhelm, M. (1999a). Vgamma9/Vdelta2 T cell activation induced by bacterial low molecular mass compounds depends on the 1-deoxy-D-xylulose 5-phosphate pathway of isoprenoid biosynthesis. FEMS Immunol Med Microbiol 25, 371-378.

Jomaa, H., Wiesner, J., Sanderbrand, S., Altincicek, B., Weidemeyer, C., Hintz, M., Turbachova, I., Eberl, M., Zeidler, J., Lichtenthaler, H. K., et al. (1999b). Inhibitors of the nonmevalonate pathway of isoprenoid biosynthesis as antimalarial drugs. Science 285, 1573-1576

Kato, Y., Tanaka, Y., Miyagawa, F., Yamashita, S., and Minato, N. (2001). Targeting of tumor cells for human gammadelta T cells by nonpeptide antigens. J Immunol 167, 5092-5098.

Knorre et al., Febs letters, 1976, 70, 105-108.

Kobayashi, H., Tanaka, Y., Yagi, J., Toma, H., and Uchiyama, T. (2001). Gamma/delta T cells provide innate immunity against renal cell carcinoma. Cancer Immunol Immunother 50, 115-124

E. M. Kosower, B. Pazhenchevsky, H. Dodiuk, H. Kanety, and D. Faust, *J. Org. Chem.*, 46, 1668 (1981)

Kunzmann, V., Bauer, E., and Wilhelm, M. (1999). Gamma/delta T-cell stimulation by pamidronate. N Engl J Med 340, 737-738.

Lang, F., Peyrat, M. A., Constant, P., Davodeau, F., David-Ameline, J., Poquet, Y., Vie, H., Fournie, J. J., and Bonneville, M. (1995). Early activation of human V gamma 9V delta 2 T cell broad cytotoxicity and TNF production by nonpeptidic mycobacterial ligands. J Immunol 154, 5986-5994.

Liu et al., Angew. Chem. Int. Ed. 1999, 38, No 9, p 1245-1247.

Mitropoulos, D., Kooi, S., Rodriguez-Villanueva, J., and Platsoucas, C. D. (1994). Characterization of fresh (uncultured) tumour-infiltrating lymphocytes (TIL) and TIL-derived T cell lines from patients with renal cell carcinoma. Clin Exp Immunol 97, 321-327.

Miyagawa, F., Tanaka, Y., Yamashita, S., and Minato, N. (2001). Essential requirement of antigen presentation by monocyte lineage cells for the activation of primary human gamma delta T cells by aminobisphosphonate antigen. J Immunol 166, 5508-5514.

Morita, C. T., Beckman, E. M., Bukowski, J. F., Tanaka, Y., Band, H., Bloom, B. R., Golan, D. E., and Brenner, M. B. (1995). Direct presentation of nonpeptide prenyl pyrophosphate antigens to human gamma delta T cells. Immunity 3, 495-507.

Nikolaides et al, Conversion Of Amines To Phosphoesters: Decyl Diethyl Phosphate, Organic Syntheses, CV 9, 194

Nilsson et al., Acta Chemica Scandinavia B 35, 1981, p 19-27.

Nilsson and Mosbach, Eur. J. Biochem., 1980, vol. 112, p 397-402.

Poccia, F., Cipriani, B., Vendetti, S., Colizzi, V., Poquet, Y., Battistini, L., Lopez-Botet, M., Fournie, J. J., and Gougeon, M. L. (1997a). CD94/NKG2 inhibitory receptor complex modulates both anti-viral and anti-tumoral responses of polyclonal phosphoantigen-reactive V gamma 9V delta 2 T lymphocytes. J Immunol 159, 6009-6017.

Poccia, F., Malkovsky, M., Gougeon, M. L., Bonneville, M., Lopez-Botet, M., Fournie, J. J., and Colizzi, V. (1997b). Gammadelta T cell activation or anergy during infections: the role of nonpeptidic TCR ligands and BLA class I molecules. J Leukoc Biol 62, 287-291.

Poquet, Y., Kroca, M., Halary, F., Stenmark, S., Peyrat, M. A., Bonneville, M., Fournie, J. J., and Sjostedt, A. (1998). Expansion of Vgamma9 Vdelta2 T cells is triggered by *Francisella tularensis*-derived phosphoantigens in tularemia but not after tularemia vaccination. Infect Immun 66, 2107-2114.

Rohmer, M., Knani, M., Simonin, P., Sutter, B., and Sahm, H. (1993). Isoprenoid biosynthesis in bacteria: a novel pathway for the early steps leading to isopentenyl diphosphate. Biochem J 295 (Pt 2), 517-524.

Rojas, R. E., Torres, M., Fournie, J. J., Harding, C. V., and Boom, W. H. (2002). Phosphoantigen presentation by macrophages to *mycobacterium tuberculosis*-reactive Vgamma9Vdelta2+T cells: modulation by chloroquine. Infect Immun 70, 4019-4027.

Sato, E., Yoshikawa, M., and Kanaoka, Y. *Chem. Pharm. Bull*, 38(8), 2287-2289 (1990)

Seghal, D, Vijay, I. K., *Anal Biochem,* 218, 87 (1994)

Selin, L. K., Stewart, S., Shen, C., Mao, H. Q., and Wilkins, J. A. (1992). Reactivity of gamma delta T cells induced by the tumour cell line RPMI 8226: functional heterogeneity of clonal populations and role of GroEL heat shock proteins. Scand J Immunol 36, 107-117.

Shen, Y., Zhou, D., Qiu, L., Lai, X., Simon, M., Shen, L., Kou, Z., Wang, Q., Jiang, L., Estep, J., et al. (2002). Adaptive immune response of Vgamma2Vdelta2+T cells during mycobacterial infections. Science 295, 2255-2258.

Sicard, H., Al Saati, T., Delsol, G., and Fournie, J. J. (2001). Synthetic phosphoantigens enhance human Vgamma9Vdelta2 T lymphocytes killing of non-Hodgkin's B lymphoma. Mol Med 7, 711-722.

Sturm, E., Braakman, E., Fisch, P., Vreugdenhil, R. J., Sondel, P., and Bolhuis, R. L. (1990). Human V gamma 9-V delta 2 T cell receptor-gamma delta lymphocytes show specificity to Daudi Burkitt's lymphoma cells. J Immunol 145, 3202-3208.

Tanaka, Y., Morita, C. T., Nieves, E., Brenner, M. B., and Bloom, B. R. (1995). Natural and synthetic non-peptide antigens recognized by human gamma delta T cells. Nature 375, 155-158.

Valentijn; G. A. van der Marel; L. H. Cohen; J. H. van Boom, *Synlett* 1991, 663-664.

A. R. P. M. Valentijn; O. van der Berg, G. A. van der Marel; L. H. Cohen; J. H. van Boom, *Tetrahedron, vol.* 51-7, 1995, 2099-2108.

Wilhelm, M., Kunzmann, V., Eckstein, S., Reimer, P., Weissinger, F., Ruediger, T., and Tony, H. P. (2003). {gamma}{delta} T cells for immune therapy of patients with lymphoid malignancies. Blood.

Yamaguchi, T., Fujimiya, Y., Suzuki, Y., Katakura, R., and Ebina, T. (1997). A simple method for the propagation and purification of gamma delta T cells from the peripheral blood of glioblastoma patients using solid-phase anti-CD3 antibody and soluble IL-2. J Immunol Methods 205, 19-28.

Zhang Donglu and Poulter C. Dale "Analysis and Purification of Phosphorylated Isoprenoids by Reversed-Phase HPLC", *Analytical Biochemistry, vol.* 213, 356-361 (1993)

Zheng, B., Lam, C., Im, S., Huang, J., Luk, W., Lau, S. Y., Yau, K. K., Wong, C., Yao, K., and Ng, M. H. (2001a). Distinct tumour specificity and IL-7 requirements of CD56(−) and CD56(+) subsets of human gamma delta T cells. Scand J Immunol 53, 40-48.

Zheng, B. J., Chan, K. W., Im, S., Chua, D., Sham, J. S., Tin, P. C., He, Z. M., and Ng, M. H. (2001b). Anti-tumor effects of human peripheral gammadelta T cells in a mouse tumor model. Int J Cancer 92, 421-425.

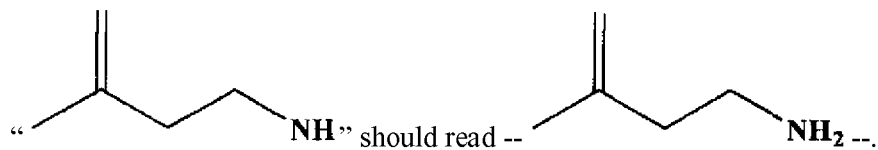

The invention claimed is:

1. A compound selected from:

Formula (X)

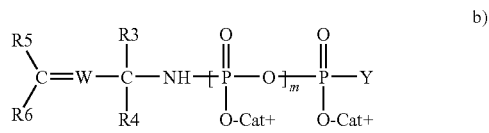

a)

in which $R_3$, $R_4$, and $R_5$, identical or different, are a hydrogen or $(C_1-C_3)$alkyl group, W is —CH— or —N—, $R_6$ is a $(C_2-C_3)$acyl, an aldehyde, a $(C_1-C_3)$alcohol, or a $(C_2-C_3)$ester, Cat+ represents $H^+$, $Na^+$, $NH_4^+$, $K^+$, $Li^+$, $(CH_3CH_2)_3NH^+$, lysine or any other suitable pharmaceutically acceptable cation, B is O or NH, m is an integer from 1 to 3, and Y is $O^-Cat+$, a nucleoside, or a radical -A-R, wherein A is O, NH, CHF, $CF_2$ or $CH_2$, and R is selected from the group consisting of:

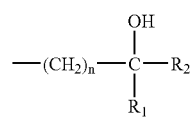

wherein n is an integer from 2 to 20, $R_1$ is a $(C_1-C_3)$alkyl group, and $R_2$ is a halogenated $(C_1-C_3)$alkyl, a $(C_1-C_3)$alkoxy-$(C_1-C_3)$alkyl, a halogenated $(C_2-C_3)$acyl or a $(C_1-C_3)$alkoxy-$(C_2-C_3)$acyl;

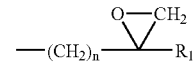

wherein n is an integer from 2 to 20, and $R_1$ is a methyl or ethyl group; and

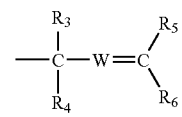

wherein $R_3$, $R_4$, and $R_5$, identical or different, are a hydrogen or $(C_1-C_3)$alkyl group, W is —CH— or —N—, and $R_6$ is a $(C_2-C_3)$acyl, an aldehyde, a $(C_1-C_3)$alcohol, or a $(C_2-C_3)$ester;

Formula (XI)

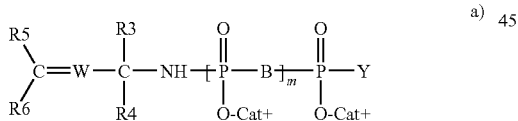

b)

in which $R_3$, $R_4$, and $R_5$, identical or different, are a hydrogen or $(C_1-C_3)$alkyl group, W is —CH— or —N—, $R_6$ is a $(C_2-C_3)$acyl, an aldehyde, a $(C_1-C_3)$alcohol, or a $(C_2-C_3)$ester, Cat+ represents $H^+$, $Na^+$, $NH_4^+$, $K^+$, $Li^+$, $(CH_3CH_2)_3NH^+$, lysine or any other suitable pharmaceutically acceptable cation, B is O or NH, m is an integer from 1 to 3, and Y is $O^-Cat+$, a nucleoside, or a radical -A-R, wherein A is O, NH, CHF, $CF_2$ or $CH_2$, and R is selected from the group consisting of:

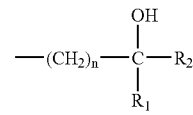

wherein n is an integer from 2 to 20, $R_1$ is a $(C_1-C_3)$alkyl group, and $R_2$ is a halogenated $(C_1-C_3)$alkyl, a $(C_1-C_3)$alkoxy-$(C_1-C_3)$alkyl, a halogenated $(C_2-C_3)$acyl or a $(C_1-C_3)$alkoxy-$(C_2-C_3)$acyl;

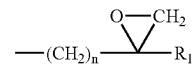

wherein n is an integer from 2 to 20, and $R_1$ is a methyl or ethyl group; and

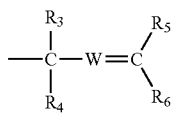

wherein $R_3$, $R_4$, and $R_5$, identical or different, are a hydrogen or $(C_1-C_3)$alkyl group, W is —CH— or —N—, and $R_6$ is a $(C_2-C_3)$acyl, an aldehyde, a $(C_1-C_3)$alcohol, or a $(C_2-C_3)$ester; or Formula (XII)

c)

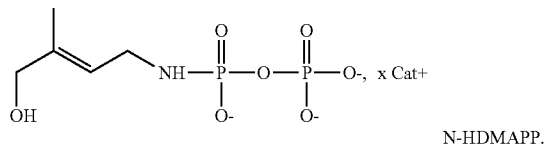

N-HDMAPP.

2. A composition comprising a carrier and a compound selected from:

Formula (X)

i)

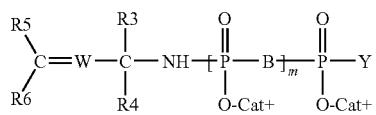

in which $R_3$, $R_4$, and $R_5$, identical or different, are a hydrogen or $(C_1-C_3)$alkyl group, W is —CH— or —N—, $R_6$ is a $(C_2-C_3)$acyl, an aldehyde, a $(C_1-C_3)$alcohol, or a $(C_2-C_3)$ester, Cat+ represents $H^+$, $Na^+$, $NH_4^+$, $K^+$, $Li^+$, $(CH_3CH_2)_3NH^+$, lysine or any other suitable pharmaceutically acceptable cation, B is O or NH, m is an integer from 1 to 3, and Y is $O^-Cat+$, a nucleoside, or a radical -A-R, wherein A is O, NH, CHF, $CF_2$ or $CH_2$, and R is selected from the group consisting of:

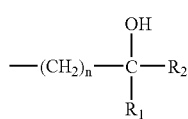

wherein n is an integer from 2 to 20, $R_1$ is a $(C_1-C_3)$alkyl group, and $R_2$ is a halogenated $(C_1-C_3)$alkyl, a $(C_1-C_3)$alkoxy-$(C_1-C_3)$alkyl, a halogenated $(C_2-C_3)$acyl or a $(C_1-C_3)$alkoxy-$(C_2-C_3)$acyl;

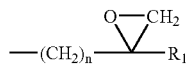

wherein n is an integer from 2 to 20, and $R_1$ is a methyl or ethyl group; and

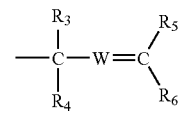

wherein $R_3$, $R_4$, and $R_5$, identical or different, are a hydrogen or $(C_1-C_3)$alkyl group, W is —CH— or —N—, and $R_6$ is a $(C_2-C_3)$acyl, an aldehyde, a $(C_1-C_3)$alcohol, or a $(C_2-C_3)$ester;

Formula (XI)

ii)

in which $R_3$, $R_4$, and $R_5$, identical or different, are a hydrogen or $(C_1-C_3)$alkyl group, W is —CH— or —N—, $R_6$ is a $(C_2-C_3)$acyl, an aldehyde, a $(C_1-C_3)$alcohol, or a $(C_2-C_3)$ester, Cat+ represents $H^+$, $Na^+$, $NH_4^+$, $K^+$, $(CH_3CH_2)_3NH^+$, lysine or any other suitable pharmaceutically acceptable cation, B is O or NH, m is an integer from 1 to 3, and Y is $O^-Cat+$, a nucleoside, or a radical -A-R, wherein A is O, NH, CHF, $CF_2$ or $CH_2$, and R is selected from the group consisting of:

wherein n is an integer from 2 to 20, $R_1$ is a $(C_1-C_3)$alkyl group, and $R_2$ is a halogenated $(C_1-C_3)$alkyl, a $(C_1-C_3)$alkoxy-$(C_1-C_3)$alkyl, a halogenated $(C_2-C_3)$acyl or a $(C_1-C_3)$alkoxy-$(C_2-C_3)$acyl;

wherein n is an integer from 2 to 20, and $R_1$ is a methyl or ethyl group; and wherein $R_3$, $R_4$, and $R_5$, identical or different, are a hydrogen or $(C_1-C_3)$alkyl group, W is —CH— or —N—, and $R_6$ is a $(C_2-C_3)$acyl, an aldehyde, a $(C_1-C_3)$alcohol, or a $(C_2-C_3)$ester; or Formula (XII)

iii)

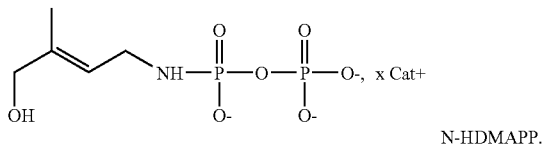

N-HDMAPP.

3. The composition according to claim 2, wherein said compound is:

Formula (XII)

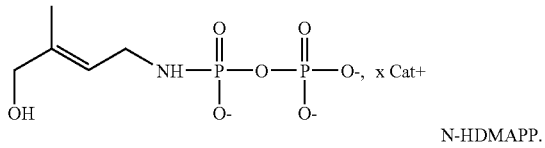

N-HDMAPP.

4. The composition according to claim 3, wherein said carrier is an adjuvant.

5. The composition according to claim 4, wherein said composition of matter further comprises an antigen selected from a microbial antigen, a viral antigen, a bacterial antigen, a fungal antigen, a protozoan antigen, a yeast antigen, a parasite antigen, a *Mycobacterium bovis* antigen or a tumoral antigen.

6. The composition according to claim 3, wherein said carrier is a pharmaceutically acceptable carrier.

7. A method of activating a γδ T cell, the method comprising bringing a γδ T cell into contact with a composition comprising a pharmaceutically acceptable carrier and a compound according to claim 1.

8. The method according to claim 7 wherein the γδ T cell is brought into contact with said γδ T cell activator in vitro.

9. A method of immunotherapy or stimulation of an immune response comprising the administration of a composition comprising a pharmaceutically acceptable carrier and a compound according to claim 1 to a subject having a tumor, solid tumor or an infectious disease.

10. The method according to claim 9, wherein said subject is suffering from a tumor.

11. The method according to claim 9, wherein said subject is suffering from a solid tumor.

12. The method according to claim 9, wherein said subject is suffering from an infectious disease.

13. The method according to claim 9, wherein said composition further comprises an antigen.

14. The method according to claim 13, wherein said antigen is selected from a microbial antigen, a viral antigen, a bacterial antigen, a fungal antigen, a protozoan antigen, a yeast antigen, a parasite antigen, a *Mycobacterium bovis* antigen or a tumoral antigen.

* * * * *

UNITED STATES PATENT AND TRADEMARK OFFICE
CERTIFICATE OF CORRECTION

PATENT NO. : 7,767,842 B2
APPLICATION NO. : 10/581144
DATED : August 3, 2010
INVENTOR(S) : Christian Belmant and Patrice Nury It is certified that error appears in the above-identified patent and that said Letters Patent is hereby corrected as shown below:

Column 2,
Line 36, "circulating 75 T cells" should read --circulating γδ T cells--.

Column 3,
Line 15, "that other compounds" should read --than other compounds--.

Column 5,
Line 54, "inventions provides" should read --invention provides--.

Column 7,
Lines 56-57, "increased in potency" should read --increased potency--.

Column 11,
Line 50,

Column 12,
Line 11, "can also be targeting" should read --can also be a targeting--.

Column 26,
Line 28, "In other aspect" should read --In another aspect--.

Column 27,
Line 54, "are simultaneously" should read --are simultaneously administered--.
Line 55, "are sequentially" should read --are sequentially administered--.

Signed and Sealed this
Eleventh Day of January, 2011

David J. Kappos
*Director of the United States Patent and Trademark Office*

CERTIFICATE OF CORRECTION (continued)
U.S. Pat. No. 7,767,842 B2

Column 32,
Line 40,

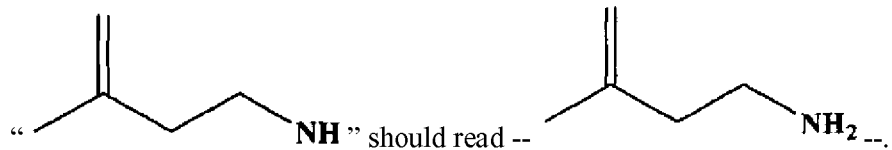

Column 34,
Line 17,

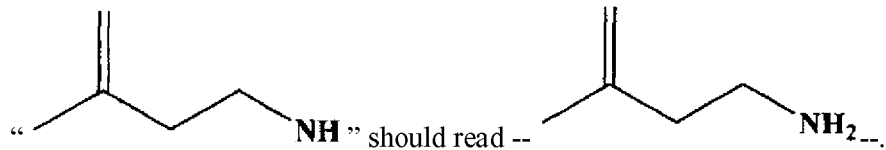

Column 34,
Line 60,